US008383658B2

(12) United States Patent
Gopalakrishnan et al.

(10) Patent No.: US 8,383,658 B2
(45) Date of Patent: Feb. 26, 2013

(54) ISOXAZOLE BASED NEURONAL NICOTINIC RECEPTOR LIGANDS AND METHODS OF USE

(75) Inventors: Murali Gopalakrishnan, Libertyville, IL (US); Jianguo Ji, Libertyville, IL (US); Chih-Hung Lee, Vernon Hills, IL (US); Tao Li, Grayslake, IL (US); Kevin B. Sippy, Antioch, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/477,291

(22) Filed: Jun. 3, 2009

(65) Prior Publication Data
US 2009/0306096 A1 Dec. 10, 2009

Related U.S. Application Data

(60) Provisional application No. 61/058,735, filed on Jun. 4, 2008.

(51) Int. Cl.
*A61K 31/42* (2006.01)
(52) U.S. Cl. ..... 514/378; 544/333; 544/405; 546/283.4; 548/247
(58) Field of Classification Search ................... 514/378; 544/333, 405; 546/283.4; 548/247
See application file for complete search history.

(56) References Cited

U.S. PATENT DOCUMENTS

| 5,914,328 | A | 6/1999 | Lin et al. |
| 5,948,793 | A | 9/1999 | Abreo et al. |
| 6,809,105 | B2 | 10/2004 | Schrimpf et al. |
| 6,833,370 | B1 | 12/2004 | Schrimpf et al. |
| 2003/0055085 | A1 | 3/2003 | Wagenen et al. |
| 2004/0186107 | A1 | 9/2004 | Schrimpf et al. |
| 2007/0010553 | A1* | 1/2007 | Lehmann ............. 514/314 |

FOREIGN PATENT DOCUMENTS

| RU | 2088229 C1 | 8/1997 |
| WO | 9932480 A1 | 7/1999 |
| WO | 0071534 A1 | 11/2000 |
| WO | 2006114400 A1 | 11/2006 |
| WO | 2008049864 A | 5/2008 |

OTHER PUBLICATIONS

Azarifar, et al. Heterocycles, 71(3), 2007, 683-689.*
Bandiera, T., et al.,"On the Oximation of Diaryl-β-diketones", J. Heterocycl. Chem., vol. 29, p. 1423-1428, 1992.
Batore, et al., "Photoinduced Ring Transformation of Pyrido-[1,2-b]pryidazinium-4-olate", Tetrahedron, vol. 50(16), pp. 4699-4708, 1994.
Beilstein Database Accession Nos. 529051, 529052, 540768, 541139, 548064, 548078; Beilstein Institute for Organic Chemistry, Frankfurt_Main, DE: abstract & Jurkowska-Kowalczyk, E: Roczniki Chemii, vol. 51, 1977; pp. 1191-1199.
Beilstein Database Accession No. 617758; Beilstein Institute for Organic Chemistry, Frankfurt_Main, DE: abstract & Giannella, M., et al.: Bollettino Chimico Farm, vol. 105, 1966, pp. 708-718.
Belgodere, E.,et al.,"Studies on Isomeric Pyridylisoxazoles", Heterocycles, vol. 20(3), pp. 501-504, 1983.
Choung, W., "4-(Isoxazol-3-yl) pyrimidines from Pyrimidinyl Nitrile Oxides", SYNLETT, No. 19, pp. 3036-3040, 2008.
Curtis, L., et al., "Potentiation of Human α4β2 Neuronal Nicotinic Acetylcholine Receptor by Estradiol", Molecular Pharmacology, vol. 61, pp. 127-135, 2002.
Decker, M. W., et al., "Nicotinic Acetylcholine Receptor Agonists: A Potential New Class of Analgesics", Curr. Top. Med. Chem., vol. 4, pp. 369-384, 2004.
Desarlo,F., et al., Isoxazolin-5-one, J. Chem. Soc. C., vol. 86, p. 86-89, 1971.
Dunbar, G.C., et al., "Effect of ispronicline, a neuronal nicotinic acetylcholine receptor partial agonist, in subjects with age associated memory impairment (AAMI)", Psychopharmacology, vol. 21, pp. 171-178, 2007.
Ferreira, M., et al., "Brainstem Nicotinic Receptor Subtypes that Influence Intragastric and Arterial Blood Pressures", J. Pharmacol. and Exp. Ther., vol. 294, pp. 230-238, 2000.
Gopalakrishnan, M., et al, Ion channels—Ligand gated. Comprehensive Medicinal Chemistry II, Edited by Triggle D.J. et al., Major Reference Works, Elsevier, Unit 2.22, pp. 877-918, 2006.
He, Y., et al., Synthesis, p. 989, Sep. 1994.
Horn, Ulrich von, "Halogenierte Pyridine III. Di-und trihalogenierte Pyridin-3-aldehyde", Helvetica Chimica Acta, vol. 59, Fasc. 1, pp. 211-221, 1976.
Jones, R.C., F., et al., "1,3-Dipolar cycloaddition route to oxygen heterocyclic triones", J. Chem. Soc. Perkin Trans., Journal of the Chemical Society. Perkin transactions 1 (0300-922X) vol. 1, p. 411, 1998.
Johnston, K. Met al., "The Conversion of Some α-Acetylenic Ketones and the Related αβ-Dibromoketones into 3,5-Diarylisoxazoles", J. Chem., Soc. C, vol. 1774-1777, 1968.
Kim, J.N., et al., "Synthesis of 4-Acylisoxazole-5-Carboxylates via 1,3-DI-Polar cycloadditoin Reaction of βAcylpyruvates with Nitrile Oxides in the Absence of Base", Heterocycles, vol. 31, p. 663-670, 1990.
Ku, Y.Y. et al., Org. Lett., "Use of Iodoacetylene as a Dipolarphile in the Synthesis of 5-Iodoisoxazole Derivates", vol. 3 (26), pp. 4185-4187, 2001.
Lauretti, G.T.,"Highlights in opioid agonists and antagonists", Expert Reviews in Neurotherapeutics, vol. 6, pp. 613-622, 2006.
Mitchell, et al., "Reactions of Benzoylheteroaroylmethanes with Hydroxylamine Hydrochloride", Tetrahedron vol. 32, pp. 2437-2438, 1976.
Nitz, T.J., et al., "Regiospecific Synthesis of 3-Substituted 5-Alkylisoxazoles from Oxime Dianions and N-Methoxy-N-methylalkylamides", J. Org. Chem., vol. 59, p. 5828-5832, 1994.

(Continued)

Primary Examiner — Douglas M Willis
(74) Attorney, Agent, or Firm — Michael Best & Friedrich LLP

(57) ABSTRACT

The invention relates to isoxazole derivatives, compositions comprising such compounds, and methods of preventing or treating conditions and disorders using such compounds and compositions.

10 Claims, No Drawings

OTHER PUBLICATIONS

Pasternack, G.W., "Pharmacological Mechanisms of Opioid Analgesics", Clin. Neuropharmacol. vol. 16, p. 1-18, 1993.

Prescott, E., Methods in Cell Biology, vol. XIV, Academic Press, New York, N.Y., p. 33 et seq., 1976.

Wakefield, B.J.,"Hetarenes and Related Ring Systems Five-Membered Hetarenes with One Chalcogen and One Additional Heteroatom", Science of Synthesis, vol. 11, 229-288, 2002, listed as Schaumann, E.

Silva, et al., "New Isoxazole Derivatives designed as Nicotinic Acetylcholine Receptor Ligand Candidates", Eur. J. Med. Chem., vol. 37, pp. 163-170, 2002.

Stephens, C.E., et al., "Nuclear fluorination of 3,5-diarylisoxazoles with Selectfluor®", J. Fluorine Chem., vol. 125, pp. 193-1945, 2004.

Furniss, Vogel's Textbook of Practical Organic Chemistry, 5th edition (1989), by Furniss, et al., Pub. Longman Scientific 7 Technical, Essex CM20 2JE, England.

Wilens, T.E., et al., "ABT-089, A Neuronal Nicotinic Receptor Partial Agonist, for the Treatment of Attention-Deficit/Hyperactivity Disorder in Adults: Results of Pilot Study", Biol. Psychiatry, vol. 59, pp. 1065-1070, 2006.

PCT Search Report and Written Opinion, PCT/US2009/046042 mailed on Jul. 15, 2009.

"Part 16: Air Interface for Fixed Broadband Wireless Access Systems" IEEE Computer Society—Oct. 2004, parts 1, 6, 8, and annex B.

* cited by examiner

ISOXAZOLE BASED NEURONAL NICOTINIC RECEPTOR LIGANDS AND METHODS OF USE

This application claims priority to the U.S. Provisional Application Ser. No. 61/058,735 filed on Jun. 4, 2008, the entirety of which is incorporated herein by reference.

BACKGROUND OF THE INVENTION

1. Technical Field

The invention relates to novel isoxazole derivatives, compositions comprising such compounds, and methods of preventing or treating conditions and disorders using such compounds and compositions.

2. Description of Related Technology

The endogenous cholinergic neurotransmitter, acetylcholine (ACh), exerts its biological effect via two types of cholinergic receptors, the muscarinic acetylcholine receptors (mAChR) and the nicotinic acetylcholine receptors (nAChR). nAChRs are pentameric assemblies of subunits surrounding a central pore that gates the flux of $Na^+$, $K^+$ and $Ca^{2+}$ ions. At least 16 subunit proteins, i.e. $\alpha 2-\alpha 10$, $\beta 1-\beta 10$, $\gamma$, $\delta$ and $\epsilon$, have been identified in neuronal tissues. These subunits provide for a great variety of homomeric and heteromeric combinations that account for the diverse receptor subtypes. For example, functional neuronal nAChR or neuronal nicotinic receptor (NNR) assemblies can be homomeric, comprising $\alpha 7$ or $\alpha 8$ or $\alpha 9$ subunits, or heteromeric, usually with at least one subunit from the $\alpha$ group ($\alpha 2$, $\alpha 3$, $\alpha 4$, $\alpha 6$) and the remainder from the $\beta$ group ($\beta 2$, $\beta 4$). In the central nervous system, $\alpha 4\beta 2$-containing NNR and $\alpha 7$-containing NNR subtypes are the most widespread and mediate synaptic and, possibly, paracrine functions. These NNRs are expressed at high levels in areas involved with learning and memory, and play key roles in modulating neurotransmission in these regions. Reduced cholinergic activity and dysregulation of NNRs have been correlated with disease states involving cognitive deficits, progressive dementia, and epilepsy. Accordingly, these NNRs are implicated in a range of physiological and patho-physiological functions related to cognitive function, learning and memory, reward, motor control, arousal and analgesia (reviewed in Gopalakrishnan, M. et al., Ion channels—Ligand-gated. Comprehensive Medicinal Chemistry II, Edited by Triggle D. J. et al., Major Reference Works, Elsevier. Unit 2.22, pp 877-918, 2006).

Discovery of the important roles played by NNRs in several CNS disorders has called attention to these membrane proteins and to ligands, or compounds, that are able to modulate, i.e. modify, the function of such membrane proteins. The prototypical NNR agonist, nicotine, has itself been shown to improve attention and cognitive performance, reduce anxiety, normalize sensory gating, and effect neuroprotection. However, nicotine is not sufficiently selective among NNRs and its utility is limited by side effects including seizures, irregular heartbeat, hypertension, and gastrointestinal effects. Accordingly, identification of compounds, agonists or allosteric modulators, that target distinct subtypes to retain the beneficial effects, while eliminating or decreasing adverse effects, continues to be an active area of research.

NNRs, especially $\alpha 4\beta 2$ NNRs, have been targeted for pain, cognitive disorders and various central nervous system diseases. Gene knockout, antisense and pharmacological studies have shown that $\alpha 4$ and $\beta 2$ NNRs are responsible for mediating nicotinic analgesia at supraspinal responses and spinal sites (Decker, M. W., et al., *Curr. Top. Med. Chem.*, 4: 369-384, 2004). Ligands targeting $\alpha 4\beta 2$ NNRs have shown improvement in cognitive and attentive function in preclinical models and, more recently, in human disease states such as attention deficit hyperactivity disorder (ADHD) (Wilens, T. E., et al., *Biol. Pscyhiatry*, 59: 1065, 2006) and age-associated memory impairment (Dunbar, G. C., et al., *Psychopharmacol.*, 21: 171, 2007). A key goal in the discovery of novel NNR compounds is to avoid ganglioinic $\alpha 3^*$ NNRs, as the dose-limiting emetic liability of nonselective compounds may be attributed to activation of $\alpha 3$ containing NNRs. $\alpha 3^*$ NNRs in the dorsal motor nucleus of the vagus and in nucleus tractus solitarius have been implicated in gastric and blood pressure responses to nicotine injected locally (Ferreira, M., et al., *J. Pharmacol. Exp. Ther.* 294:230-238, 2000).

Compounds with varying degrees of selectivity for $\alpha 4\beta 2$ NNRs over other nicotinic subtypes ($\alpha 3$, $\alpha 7$, $\alpha 1$-containing) have been discovered over the years for the treatment of pain and a range of psychiatric and neurological disorders especially involving cognitive deficits in attention, alertness and memory. These may include those conditions that may benefit from selective enhancement of cholinergic transmission such as attention deficit, psychotic disorders, selected pain syndromes, smoking cessation and those thought to involve reduced cholinergic function such as neurodegenerative disorders, central inflammatory or autoimmune disorders, brain trauma and cerebrovascular disease. Modulation of $\alpha 4\beta 2$ NNRs is expected to be beneficial in an number of diseases including Alzheimer's disease, mild cognitive impairment and related syndromes, Lewy body dementia, vascular dementia, attention deficit/attention deficit-hyperactivity disorder, schizophrenia, bipolar and mood disorders, schizoaffective disorders, Tourette's syndrome, brain trauma, vascular dementia, Parkinson's disease, Huntington's disease and conditions of substance abuse including alcohol abuse and smoking cessation. Selected pain syndromes includes chronic pain that can be nociceptive, neuropathic, or both and originating from cancer, injury, surgery, or chronic conditions such as arthritis or nerve injury/disease. Neuropathic pain can be peripheral (painful peripheral mononeuropathy and polyneuropathy) or central (post stroke, following spinal cord injury) and can originate from nerve injury following a wide array of conditions/events such as direct trauma to nerves, inflammation/neuritis/nerve compression, metabolic diseases (diabetes), infections (herpes zoster, HIV), tumors, toxins (chemotherapy), and primary neurological diseases.

Treatment with NNR agonists, which act at the same site, as the endogenous transmitter ACh, may be problematic because ACh not only activates, but also inhibits receptor activity through processes that include desensitization. Further, prolonged receptor activation may cause long-lasting inactivation. Thus, uncertainty exists whether chronic treatment with agonists in humans might provide suboptimal benefit due to sustained receptor activation and desensitization of the NNRs. An alternate approach to target $\alpha 4\beta 2$ NNR function is by enhancing effects of the endogenous neurotransmitter acetylcholine via positive allosteric modulation. This approach provides an opportunity to (i) reinforce the endogenous cholinergic neurotransmission without directly activating the receptor like classical agonists, (ii) prevent receptor desensitization (iii) possibly resensitize inactivated receptors. Thus, the spatial and temporal characteristics of endogenous $\alpha 4\beta 2$ receptor activation are preserved unlike agonists that will tonically activate all receptors, leading to a non-physiological pattern of receptor activation.

In light of the evidence supporting the various therapeutic uses of NNRs, it would be beneficial to discover novel allosteric modulators that could provide therapeutic benefits.

SUMMARY OF THE INVENTION

The invention relates to isoxazole compounds, compositions comprising such compounds, and method of using such compounds and compositions.

In one aspect, the invention is compounds having the formula (I)

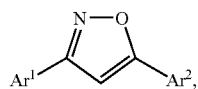

wherein $Ar^1$ and $Ar^2$ are optionally substituted aryl or heteroaryl.

Another aspect of the invention relates to pharmaceutical compositions comprising compounds of formula I. Such compositions can be administered typically as part of a therapeutic regimen for treatment or prevention of conditions and disorders related to NNR activity.

Yet another aspect of the invention relates to a method of modulating α4β2 NNR activity. The method is useful for treating, preventing or both treating and preventing conditions and disorders related to α4β2 NNR activity, particularly in mammals. Such method is useful for treating, preventing or both treating and preventing conditions and disorders related to α4β2 NNR activity in mammals.

A further aspect of the invention relates to a method of selectively modulating NNR activity, for example α4β2 NNR PAM activity, in combination with a nicotinic agonist or partial agonist to improve the tolerability of therapy using such nicotinic agonist or partial agonist.

Yet another aspect of the invention relates to a method for treating, preventing or both treating and preventing pain.

DETAILED DESCRIPTION OF THE INVENTION

Definition of Terms

As used throughout this specification and the appended claims, the following terms have the following meanings:

The term "acetyl" as used herein, means a —C(O)CH$_3$ group.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" as used herein, means an alkyl group, as defined herein, appended to the parent molecular moiety through an amino group, as defined herein. Representative examples of alkylamino include, but are not limited to methylamino, ethylamino, and sec-butylamino.

The term "amino" as used herein, means a —NH$_2$ group.

The term "aryl," as used herein, means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl.

The aryl groups of this invention can be substituted with 0, 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylcarbonyloxyalkyl, alkylsulfinyl, alkylsulfinylalkyl, alkylsulfonyl, alkylsulfonylalkyl, alkylthio, alkylthioalkyl, alkynyl, arylalkyl, arylalkoxy, aryloxy, carboxy, carboxyalkyl, cyano, cyanoalkyl, formyl, formylalkyl, halogen, haloalkyl, haloalkoxy, hydroxy, hydroxyalkyl, mercapto, nitro, —NZ$^1$Z$^2$, and (NZ$^3$Z$^4$)carbonyl.

The term "concurrently administering" or "concurrent administration" as used herein, refers to administering, or the administration of, respectively, an α4β2 receptor ligand to a patient, who has been prescribed (or has consumed) at least one α4β2 PAM, at an appropriate time so that the patient's symptoms may subside. This may mean simultaneous administration of an α4β2 PAM and an α4β2 receptor ligand, or administration of the medications at different, but appropriate times.

The term "cyano" as used herein, means a —CN group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, dichloromethyl, trichloromethyl, fluoromethyl, difluoromethyl, trifluoromethyl, 2-fluoroethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridin-3-yl, pyridazinyl, pyrimidinyl, pyrazinyl, pyrazolyl, pyrrolyl, tetrazolyl, thiadiazolyl, thiazolyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, quinolinyl, quinoxalinyl and thienopyridinyl, The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, and nitro. Heteroaryl groups of the invention that are substituted with a hydroxy group may be present as tautomers. The heteroaryl groups of the invention encompasses all tautomers including non-aromatic tautomers.

The term "hydroxy" or "hydroxyl" as used herein, means an —OH group.

The term "nitro" as used herein, means a —NO$_2$ group.

The term "parenterally," as used herein, refers to modes of administration, including intravenous, intramuscular, intraperitoneal, intrasternal, subcutaneous, intraarticular injection, and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate; as well as coloring agents, releasing agents, coating agents, sweetening, flavoring and perfuming agents, preservatives and antioxidants can also be present in the composition, according to the judgment of one skilled in the art of formulations.

The term "pharmaceutically acceptable salts," as used herein, include salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use. Pharmaceutically acceptable salts are well-known in the art. The salts can be prepared in situ during the final isolation and purification of the compounds of the invention, or separately by reacting a free base function with a suitable organic acid.

Also, the basic nitrogen-containing groups can be quaternized with agents as alkyl halides such as methyl, ethyl, propyl, butyl, decyl, lauryl, myristyl and stearyl chlorides, bromides and iodides; dialkyl sulfates such as dimethyl, diethyl, dibutyl and diamyl sulfates; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such. Other representative organic amines useful for the formation of base addition salts include ethylenediamine, ethanolamine, diethanolamine, piperidine, and piperazine.

The term "positive allosteric modulator" or PAM, as used herein, means a compound that enhances activity of an endogenous, or naturally occurring, ligand, such as but not limited to ACh, or an exogenously administered agonist. Although typically it may be recognized that an asterisk is used to indicate that the exact subunit composition of a receptor is uncertain, for example α4β2* indicates a receptor that contains the α4 and β2 subunits proteins in combination with other subunits.

The term "tautomer" as used herein means a proton shift from one atom of a compound to another atom of the same compound wherein two or more structurally distinct compounds are in equilibrium with each other.

Compounds of the Invention

An embodiment of the invention is compounds having the formula (I)

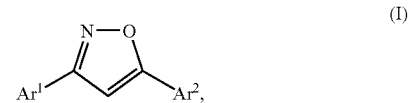

wherein Ar$^1$ and Ar$^2$ are optionally substituted aryl or heteroaryl.

In one embodiment of the invention, suitable heteroaryl groups include, but are not limited to, pyridinyl, pyrazinyl, pyridazinyl, pyrimidinyl, and triazinyl; and examples of suitable substituents can include, but are not limited to acetyl, alkoxy, alkyl, alkylamino, amino, cyano, halo, haloalkyl, hydroxy, and nitro.

In another embodiment of the invention, suitable aryl groups include, but are not limited to, phenyl.

Another embodiment of the invention is a compound of formula (I), wherein Ar$^1$ and Ar$^2$ are heteroaryl.

Another embodiment of the invention is a compound of formula (I), wherein Ar$^1$ and Ar$^2$ are heteroaryl, provided that Ar$^1$ and Ar$^2$ are not the same heteroaryl.

Another embodiment of the invention is a compound of formula (I), wherein Ar$^1$ and Ar$^2$ are heteroaryl, provided that at least one of them is not a pyridinyl.

Another embodiment of the invention is a compound of formula (I), wherein Ar$^1$ is pyridin-3-yl, pyrimidinyl or pyrazinyl, substituted with 0, 1, 2, or 3 substitutions selected from the group consisting of acetyl, alkoxy, alkyl, alkylamino, amino, cyano, halo, haloalkoxy, haloalkyl, hydroxy, and nitro;

Ar$^2$ is phenyl, substituted with 0, 1, 2, or 3 substitutions selected from the group consisting of acetyl, alkoxy, alkyl, alkylamino, amino, cyano, halo, haloalkoxy, haloalkyl, hydroxy, and nitro;

or a pharmaceutically acceptable salt thereof.

Another embodiment of the invention is a compound of formula (I), wherein Ar$^1$ is optionally substituted pyridin-3-yl, and Ar$^2$ is optionally substituted phenyl.

Another embodiment of the invention is a compound of formula (I), wherein $Ar^1$ and $Ar^2$ are optionally substituted pyridin-3-yl.

In another embodiment, the compounds of the invention can have the formula (I), wherein $Ar^1$ is optionally substituted pyridin-3-yl, and $Ar^2$ is optionally substituted pyrazinyl or pyridazinyl.

In another embodiment, the compounds of the invention can have the formula (I), wherein $Ar^1$ is optionally substituted pyrazinyl and $Ar^2$ is optionally substituted phenyl.

Another embodiment of the invention is compounds of formula (I), wherein $Ar^1$ is optionally substituted pyrimidinyl and $Ar^2$ is optionally substituted phenyl.

Various embodiments of the invention described herein include, but are not limited to, pharmaceutically acceptable salts thereof.

Another embodiment of the invention is a compound of formula I, or a pharmaceutically acceptable salt thereof, selected from the group of compounds exemplified in Examples 1-96 below.

Another embodiment of the invention is a compound of formula I, or a pharmaceutically acceptable salt thereof, selected from the group of compounds exemplified in 2-17, 19-25, 27, 29-43, 45-59, 67-68, 70-82, and 84-95 below.

Another embodiment of the invention is a compound of formula I, or a pharmaceutically acceptable salt thereof, selected from the group of compounds exemplified in Examples 2-17, 19-25 and 67-68 below.

Another embodiment of the invention is a compound of formula I, or a pharmaceutically acceptable salt thereof, selected from the group of compounds exemplified in Examples 29-43 and 60-66 below.

Another embodiment of the invention is a compound of formula I, or a pharmaceutically acceptable salt thereof, selected from the group of compounds exemplified in Examples 45-59 below.

Another embodiment of the invention is a compound of formula I, or a pharmaceutically acceptable salt thereof, selected from the group of compounds exemplified in Examples 70-82 and 95-96 below.

Another embodiment of the invention is a compound of formula I, or a pharmaceutically acceptable salt thereof, selected from the group of compounds exemplified in Examples 84-94 below.

Another embodiment of the invention is a compound of formula I, or a pharmaceutically acceptable salt thereof, selected from the group of compounds exemplified in Examples 1, 26-28, 44, 69, and 83 below.

Another embodiment of the invention is a compound of formula I, or a pharmaceutically acceptable salt thereof, selected from the group of compounds exemplified in Examples 18, 26-28, 44, 69, and 83 below.

Another embodiment of the invention is a compound of formula I, or a pharmaceutically acceptable salt thereof, selected from the group of compounds exemplified in Examples 26-28, 44, 69, and 83 below.

Further embodiments of the invention described below, which, taken alone or together, are representative compounds of the formula I.

Another embodiment of the invention is 3,5-di(pyridin-3-yl)isoxazole, or a pharmaceutically acceptable salt thereof.

Another embodiment of the invention is 5-(3,4-dichlorophenyl)-3-(pyridin-3-yl)isoxazole, or a pharmaceutically acceptable salt thereof.

Another embodiment of the invention is 5-(4-fluoro-3-methylphenyl)-3-(pyridin-3-yl)isoxazole, or a pharmaceutically acceptable salt thereof.

Another embodiment of the invention is 5-(3-fluoro-4-(trifluoromethoxy)phenyl)-3-(pyridin-3-yl)isoxazole, or a pharmaceutically acceptable salt thereof.

Another embodiment of the invention is 4-(3-(pyridin-3-yl)isoxazol-5-yl)benzonitrile, or a pharmaceutically acceptable salt thereof.

Another embodiment of the invention is 5-(4-fluorophenyl)-3-(pyridin-3-yl)isoxazole, or a pharmaceutically acceptable salt thereof.

Another embodiment of the invention is 5-(3,5-difluorophenyl)-3-(pyridin-3-yl)isoxazole, or a pharmaceutically acceptable salt thereof.

Another embodiment of the invention is 5-(4-bromophenyl)-3-(pyridin-3-yl)isoxazole, or a pharmaceutically acceptable salt thereof.

Another embodiment of the invention is 3-(pyridin-3-yl)-5-(3-(trifluoromethyl)phenyl)isoxazole, or a pharmaceutically acceptable salt thereof.

Another embodiment of the invention is 5-(3-fluorophenyl)-3-(pyridin-3-yl)isoxazole, or a pharmaceutically acceptable salt thereof.

Another embodiment of the invention is 5-(4-chlorophenyl)-3-(pyridin-3-yl)isoxazole, or a pharmaceutically acceptable salt thereof.

Another embodiment of the invention is 5-(3,5-dimethoxyphenyl)-3-(pyridin-3-yl)isoxazole, or a pharmaceutically acceptable salt thereof.

Another embodiment of the invention is 3-(pyridin-3-yl)-5-m-tolylisoxazole, or a pharmaceutically acceptable salt thereof.

Another embodiment of the invention is 5-(2,4-difluorophenyl)-3-(pyridin-3-yl)isoxazole, or a pharmaceutically acceptable salt thereof.

Another embodiment of the invention is 5-(2-fluorophenyl)-3-(pyridin-3-yl)isoxazole, or a pharmaceutically acceptable salt thereof.

Another embodiment of the invention is 5-(3,4-difluorophenyl)-3-(pyridin-3-yl)isoxazole, or a pharmaceutically acceptable salt thereof.

Another embodiment of the invention is 5-(3,4,5-trifluorophenyl)-3-(pyridin-3-yl)isoxazole, or a pharmaceutically acceptable salt thereof.

Another embodiment of the invention is 3-(5-(pyridin-3-yl)isoxazol-3-yl)benzonitrile, or a pharmaceutically acceptable salt thereof.

Another embodiment of the invention is 3-(3-(pyridin-3-yl)isoxazol-5-yl)benzonitrile, or a pharmaceutically acceptable salt thereof.

Another embodiment of the invention is 5-(3-chlorophenyl)-3-(pyridin-3-yl)isoxazole, or a pharmaceutically acceptable salt thereof.

Another embodiment of the invention is 3-(pyridin-3-yl)-5-p-tolylisoxazole, or a pharmaceutically acceptable salt thereof.

Another embodiment of the invention is 5-phenyl-3-(pyridin-3-yl)isoxazole, or a pharmaceutically acceptable salt thereof.

Another embodiment of the invention is 5-(2-chlorophenyl)-3-(pyridin-3-yl)isoxazole, or a pharmaceutically acceptable salt thereof.

Another embodiment of the invention is 5-(3-aminophenyl)-3-(pyridin-3-yl)isoxazole, or a pharmaceutically acceptable salt thereof.

Another embodiment of the invention is 1-(3-(3-(pyridin-3-yl)isoxazol-5-yl)phenyl)ethanone, or a pharmaceutically acceptable salt thereof.

Another embodiment of the invention is 3-(pyridin-2-yl)-5-(pyridin-3-yl)isoxazole, or a pharmaceutically acceptable salt thereof.

Another embodiment of the invention is 5-(3-(pyridin-2-yl)isoxazol-5-yl)nicotinonitrile, or a pharmaceutically acceptable salt thereof.

Another embodiment of the invention is 3-(5-fluoropyridin-3-yl)-5-(pyridin-3-yl)isoxazole, or a pharmaceutically acceptable salt thereof.

Another embodiment of the invention is 3-(3-(5-fluoropyridin-3-yl)isoxazol-5-yl)benzonitrile, or a pharmaceutically acceptable salt thereof.

Another embodiment of the invention is 5-(3-fluorophenyl)-3-(5-fluoropyridin-3-yl)isoxazole, or a pharmaceutically acceptable salt thereof.

Another embodiment of the invention is 5-(4-chlorophenyl)-3-(5-fluoropyridin-3-yl)isoxazole, or a pharmaceutically acceptable salt thereof.

Another embodiment of the invention is 4-(3-(5-fluoropyridin-3-yl)isoxazol-5-yl)benzonitrile, or a pharmaceutically acceptable salt thereof.

Another embodiment of the invention is 5-(4-bromophenyl)-3-(5-fluoropyridin-3-yl)isoxazole, or a pharmaceutically acceptable salt thereof.

Another embodiment of the invention is 5-(3,4-dichlorophenyl)-3-(5-fluoropyridin-3-yl)isoxazole, or a pharmaceutically acceptable salt thereof.

Another embodiment of the invention is 5-(3,5-difluorophenyl)-3-(5-fluoropyridin-3-yl)isoxazole, or a pharmaceutically acceptable salt thereof.

Another embodiment of the invention is 3-(5-fluoropyridin-3-yl)-5-(3,4,5-trifluorophenyl)isoxazole, or a pharmaceutically acceptable salt thereof.

Another embodiment of the invention is 3-(5-fluoropyridin-3-yl)-5-(4-fluorophenyl)isoxazole, or a pharmaceutically acceptable salt thereof.

Another embodiment of the invention is 5-(4-fluoro-3-methylphenyl)-3-(5-fluoropyridin-3-yl)isoxazole, or a pharmaceutically acceptable salt thereof.

Another embodiment of the invention is 3-(5-fluoropyridin-3-yl)-5-(3-(trifluoromethyl)phenyl)isoxazole, or a pharmaceutically acceptable salt thereof.

Another embodiment of the invention is 3-(5-fluoropyridin-3-yl)-5-(3-methylphenyl)isoxazole, or a pharmaceutically acceptable salt thereof.

Another embodiment of the invention is 5-(3-fluoro-4-(trifluoromethoxy)phenyl)-3-(5-fluoropyridin-3-yl)isoxazole, or a pharmaceutically acceptable salt thereof.

Another embodiment of the invention is 3-(3-(5-fluoropyridin-3-yl)isoxazol-5-yl)aniline, or a pharmaceutically acceptable salt thereof.

Another embodiment of the invention is 5-(2-chlorophenyl)-3-(5-fluoropyridin-3-yl)isoxazole, or a pharmaceutically acceptable salt thereof.

Another embodiment of the invention is 5-(pyridin-3-yl)-3-(pyrimidin-5-yl)isoxazole, or a pharmaceutically acceptable salt thereof.

Another embodiment of the invention is 3-(3-(pyrimidin-5-yl)isoxazol-5-yl)benzonitrile, or a pharmaceutically acceptable salt thereof.

Another embodiment of the invention is 5-(2,4-difluorophenyl)-3-(pyrimidin-5-yl)isoxazole, or a pharmaceutically acceptable salt thereof.

Another embodiment of the invention is 3-(pyrimidin-5-yl)-5-(3,4,5-trifluorophenyl)isoxazole, or a pharmaceutically acceptable salt thereof.

Another embodiment of the invention is 4-(3-(pyrimidin-5-yl)isoxazol-5-yl)benzonitrile, or a pharmaceutically acceptable salt thereof.

Another embodiment of the invention is 5-(3,5-difluorophenyl)-3-(pyrimidin-5-yl)isoxazole, or a pharmaceutically acceptable salt thereof.

Another embodiment of the invention is 5-(3-fluorophenyl)-3-(pyrimidin-5-yl)isoxazole, or a pharmaceutically acceptable salt thereof.

Another embodiment of the invention is 5-(4-bromophenyl)-3-(pyrimidin-5-yl)isoxazole, or a pharmaceutically acceptable salt thereof.

Another embodiment of the invention is 5-phenyl-3-(pyrimidin-5-yl)isoxazole, or a pharmaceutically acceptable salt thereof.

Another embodiment of the invention is 5-(4-chlorophenyl)-3-(pyrimidin-5-yl)isoxazole or a pharmaceutically acceptable salt thereof.

Another embodiment of the invention is 5-(3,4-difluorophenyl)-3-(pyrimidin-5-yl)isoxazole or a pharmaceutically acceptable salt thereof.

Another embodiment of the invention is 3-(pyrimidin-5-yl)-5-p-tolylisoxazole or a pharmaceutically acceptable salt thereof.

Another embodiment of the invention is 5-(3,4-dichlorophenyl)-3-(pyrimidin-5-yl)isoxazole or a pharmaceutically acceptable salt thereof.

Another embodiment of the invention is 5-(3-(difluoromethoxy)phenyl)-3-(pyrimidin-5-yl)isoxazole or a pharmaceutically acceptable salt thereof.

Another embodiment of the invention is 5-(4-fluorophenyl)-3-(pyrimidin-5-yl)isoxazole or a pharmaceutically acceptable salt thereof.

Another embodiment of the invention is 3-(pyrimidin-5-yl)-5-m-tolylisoxazole or a pharmaceutically acceptable salt thereof.

Another embodiment of the invention is 4-(3-(5-fluoropyridin-3-yl)isoxazol-5-yl)phthalonitrile or a pharmaceutically acceptable salt thereof.

Another embodiment of the invention is 3-(5-fluoropyridin-3-yl)-5-phenylisoxazole or a pharmaceutically acceptable salt thereof.

Another embodiment of the invention is 5-(2-chlorophenyl)-3-(5-fluoropyridin-3-yl)isoxazole or a pharmaceutically acceptable salt thereof.

Another embodiment of the invention is 1-(3-(3-(5-fluoropyridin-3-yl)isoxazol-5-yl)phenyl)ethanone or a pharmaceutically acceptable salt thereof.

Another embodiment of the invention is 5-(3-(difluoromethoxy)phenyl)-3-(5-fluoropyridin-3-yl)isoxazole or a pharmaceutically acceptable salt thereof.

Another embodiment of the invention is 5-(3,5-dimethoxyphenyl)-3-(5-fluoropyridin-3-yl)isoxazole or a pharmaceutically acceptable salt thereof.

Another embodiment of the invention is 3-chloro-5-(3-(5-fluoropyridin-3-yl)isoxazol-5-yl)benzonitrile or a pharmaceutically acceptable salt thereof.

Another embodiment of the invention is 3-chloro-5-(3-(pyridin-3-yl)isoxazol-5-yl)benzonitrile or a pharmaceutically acceptable salt thereof.

Another embodiment of the invention is 2-fluoro-5-(3-(pyridin-3-yl)isoxazol-5-yl)benzonitrile or a pharmaceutically acceptable salt thereof.

Another embodiment of the invention is 3-(5-chloropyridin-3-yl)-5-(pyridin-3-yl)isoxazole or a pharmaceutically acceptable salt thereof.

Another embodiment of the invention is 3-(5-chloropyridin-3-yl)-5-(3,4-dichlorophenyl)isoxazole or a pharmaceutically acceptable salt thereof.

Another embodiment of the invention is 3-(5-chloropyridin-3-yl)-5-(2,4-difluorophenyl)isoxazole, or a pharmaceutically acceptable salt thereof.

Another embodiment of the invention is 5-(4-chlorophenyl)-3-(5-chloropyridin-3-yl)isoxazole, or a pharmaceutically acceptable salt thereof.

Another embodiment of the invention is 4-(3-(5-chloropyridin-3-yl)isoxazol-5-yl)benzonitrile, or a pharmaceutically acceptable salt thereof.

Another embodiment of the invention is 3-(5-chloropyridin-3-yl)-5-(3,5-difluorophenyl)isoxazole, or a pharmaceutically acceptable salt thereof.

Another embodiment of the invention is 3-(5-chloropyridin-3-yl)-5-(3,4,5-trifluorophenyl)isoxazole or a pharmaceutically acceptable salt thereof.

Another embodiment of the invention is 3-(5-chloropyridin-3-yl)-5-p-tolylisoxazole or a pharmaceutically acceptable salt thereof.

Another embodiment of the invention is 3-(5-chloropyridin-3-yl)-5-(3,4-difluorophenyl)isoxazole or a pharmaceutically acceptable salt thereof.

Another embodiment of the invention is 3-(5-chloropyridin-3-yl)-5-(4-fluorophenyl)isoxazole or a pharmaceutically acceptable salt thereof.

Another embodiment of the invention is 5-(3-chlorophenyl)-3-(5-chloropyridin-3-yl)isoxazole or a pharmaceutically acceptable salt thereof.

Another embodiment of the invention is 3-(5-chloropyridin-3-yl)-5-phenylisoxazole or a pharmaceutically acceptable salt thereof.

Another embodiment of the invention is 3-(5-chloropyridin-3-yl)-5-m-tolylisoxazole or a pharmaceutically acceptable salt thereof.

Another embodiment of the invention is 3-(5-chloropyridin-3-yl)-5-(4-fluoro-3-methylphenyl)isoxazole or a pharmaceutically acceptable salt thereof.

Another embodiment of the invention is 3-(pyrazin-2-yl)-5-(pyridin-3-yl)isoxazole or a pharmaceutically acceptable salt thereof.

Another embodiment of the invention is 3-chloro-5-(3-(pyrazin-2-yl)isoxazol-5-yl)benzonitrile or a pharmaceutically acceptable salt thereof.

Another embodiment of the invention is 2-fluoro-5-(3-(pyrazin-2-yl)isoxazol-5-yl)benzonitrile or a pharmaceutically acceptable salt thereof.

Another embodiment of the invention is 3-(3-(pyrazin-2-yl)isoxazol-5-yl)benzonitrile or a pharmaceutically acceptable salt thereof.

Another embodiment of the invention is 5-(3-chlorophenyl)-3-(pyrazin-2-yl)isoxazole or a pharmaceutically acceptable salt thereof.

Another embodiment of the invention is 4-(3-(pyrazin-2-yl)isoxazol-5-yl)benzonitrile or a pharmaceutically acceptable salt thereof.

Another embodiment of the invention is 5-phenyl-3-(pyrazin-2-yl)isoxazole or a pharmaceutically acceptable salt thereof.

Another embodiment of the invention is 5-(3-fluorophenyl)-3-(pyrazin-2-yl)isoxazole or a pharmaceutically acceptable salt thereof.

Another embodiment of the invention is 5-(4-fluorophenyl)-3-(pyrazin-2-yl)isoxazole or a pharmaceutically acceptable salt thereof.

Another embodiment of the invention is 5-(3,4-difluorophenyl)-3-(pyrazin-2-yl)isoxazole or a pharmaceutically acceptable salt thereof.

Another embodiment of the invention is 3-(pyrazin-2-yl)-5-(3,4,5-trifluorophenyl)isoxazole or a pharmaceutically acceptable salt thereof.

Another embodiment of the invention is 1-(3-(3-(pyrazin-2-yl)isoxazol-5-yl)phenyl)ethanone or a pharmaceutically acceptable salt thereof.

Another embodiment of the invention is 3-(6-chloropyridin-3-yl)-5-(2,4-difluorophenyl)isoxazole or a pharmaceutically acceptable salt thereof.

Another embodiment of the invention is 5-(3-chlorophenyl)-3-(6-chloropyridin-3-yl)isoxazole or a pharmaceutically acceptable salt thereof.

Another embodiment of the invention includes novel intermediates described in the synthesis of Examples below.

Another embodiment of the invention includes novel methods described in the synthesis of Examples below.

Methods of Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: butyllithium (BuLi), ethyl acetate (EtOAc), ethanol (EtOH), sodium acetate (NaOAc), tetrahydrofuran (THF), triethylamine (NEt$_3$ or Et$_3$N), triphenylphosphine (PPh$_3$), methanol (MeOH), dimethylsulfoxide (DMSO), equivalents (eq.), acetic acid (HOAc), trifluoroacetic acid (TFA), palladium acetate (Pd(OAc)$_2$), acetate (OAc), potassium t-butoxide (t-BuOK), trimethylsilyl (TMS), tris(dibenzylidineacetone) palladium (0) (Pd$_2$(dba)$_3$), Dulbecco's Modified Eagle's Medium (DMEM), fetal bovine serum (FBS), N-methyl-D-glucamine (NMDG), and 4-(2-hydroxyethyl)-1-piperazineethanesulfonic acid (HEPES).

The compounds of this invention can be prepared according to the synthetic Schemes and/or Examples described. Certain groups can be substituted as described within the scope of this invention as would be known to one skilled in the art. Representative procedures are shown in, but are not limited to, Schemes 1-6.

Scheme 1

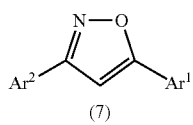

As outlined in Scheme 1, compounds of formula (1) can be reacted with 1,1'-carbonyldiimidazole (2) to furnish compounds of formula (3), which can react with the compounds of formula (4) in the presence of a base, such as but not limited to NaH or t-BuOK, to provide compounds of formula (5), wherein Ar¹ and Ar² are as defined herein. Compounds of formula (5) react with hydroxylamine to give compounds of formula (6) and/or (7) as described by Bandiera, T. et al., J. Heterocycl. Chem., 29, 1423, 1992.

in the presence of a base such as triethylamine under the catalysis of CuI and a palladium catalyst, such as but not limited to $Pd(OAc)_2$, $PdCl_2 (PPh_3)_4$ and $Pd(PPh_3)_4$, at 20-50° C. for 1-12 hours to provide compounds of formula (10) that can be treated with a base, such as but not limited to $K_2CO_3$, $Na_2CO_3$, NaOH and tetrabutylammonium chloride, to give compounds of formula (II). Compounds of formula (II) can be treated with a base such as butyllithium, then react with compounds of formula (12), wherein Ar² is as defined herein, to give compounds of formula (13). Compounds of formula (13) can be reacted with hydroxylamine to give compounds of formula (14) and/or (15) as described by Johnston, K. M et al., J. Chem. Soc. C, 1774, 1968 and De sarlo, F., et al., J. Chem. Soc. C., 86, 1971.

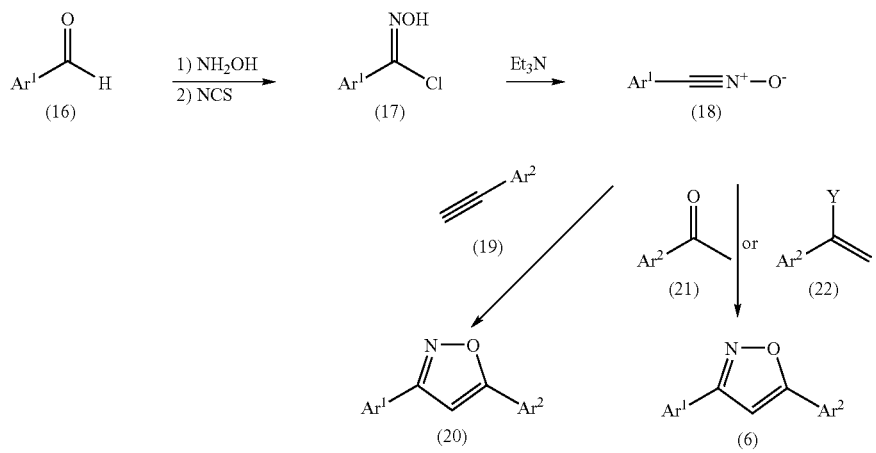

As outlined in Scheme 3, compounds of formula (16), wherein Ar¹ is as defined herein, can be reacted with hydroxylamine, and then N-chlorosuccinimide (NCS) to provide compounds of formula (17). Compounds of formula (17), when treated with a base such as $NEt_3$ or $KHCO_3$, in a solvent such as THF or dioxane, provide intermediates of formula (18). Compounds of formula (18) can react with compounds of formula (19), wherein Ar² is as defined herein, to give compounds of formula (20) as described by Denmark, S. E. et al., J. Org. Chem., 70, 2839, 2005. Alternatively, intermediates of formula (18) can react with compounds of formula (21) or (22), wherein Ar² is as defined, and Y is $OCH_3$, OAc, OTMS, $NMe_2$, Br, Cl or $NO_2$, to yield compounds of formula (6) as described by Kim, J. N. et al., Heterocycles, 31, 63, 1990 and Jones, R. C. F. et al., J. Chem. Soc. Perkin Trans. 1, 411, 1998, respectively.

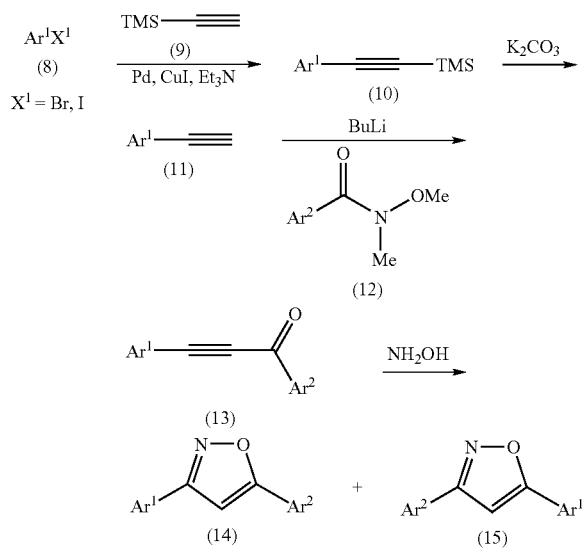

As outlined in Scheme 2, compounds of formula (8), wherein Ar¹ is as defined herein, and X¹ is bromo or iodo, can react with compounds of formula (9) in a solvent such as THF

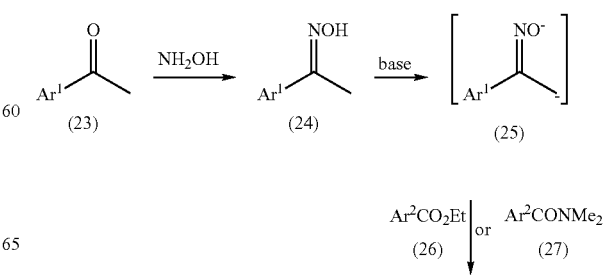

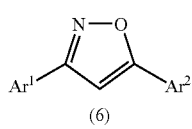

(6)

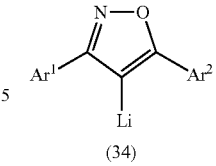

(34)

As outlined in Scheme 4, wherein $Ar^1$ and $Ar^2$ are as defined, compounds of formula (23) can be reacted with hydroxylamine to provide compounds of formula (24) that can be treated with a base, such as but not limited to butyllithium or lithium diisopropylamide, to provided the intermediate of formula (25). Intermediates of formula (25) can react with compounds of formula (26) or (27) to provide compounds of formula (6) as described in He, Y. et al., *Synthesis*, 989, 1994, and Nitz, T. J. et al., *J. Org. Chem.*, 59, 5828, 1994.

Scheme 5

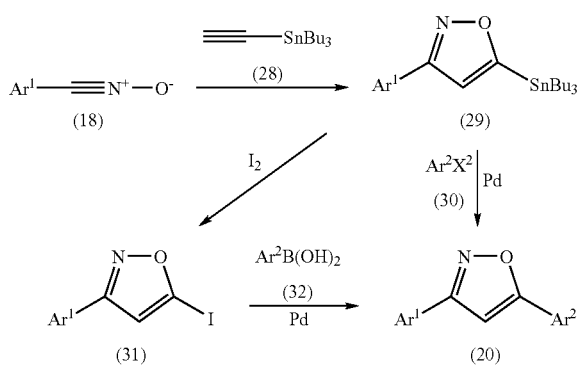

As outlined in Scheme 5, wherein $Ar^1$ and $Ar^2$ are as defined herein, compounds of formula (18), prepared as described in Scheme 3, can react with compounds of formula (28) to give compounds of formula (29). Compounds of formula (29) can react with compounds of formula (30), wherein $X^2$ is Cl, Br and I, in the presence of a palladium catalyst, such as but not limited to Pd(OAc)$_2$, PdCl$_2$(PPh$_3$)$_2$, Pd(PPh$_3$)$_4$ and Pd$_2$(dba)$_3$, to provide compounds of formula (20). Alternatively, compounds of formula (29) can be treated with iodine to provide compounds of formula (31). Compounds of formula (31) can react with compounds of formula (32), in the presence of a palladium catalyst, such as but not limited to Pd(OAc)$_2$, PdCl$_2$(PPh$_3$)$_2$, Pd(PPh$_3$)$_4$ and Pd$_2$(dba)$_3$, to provide compounds of formula (20) as described by Ku, Y-Y. et al., *Org. Lett.*, 3, 4185, 2001.

Scheme 6

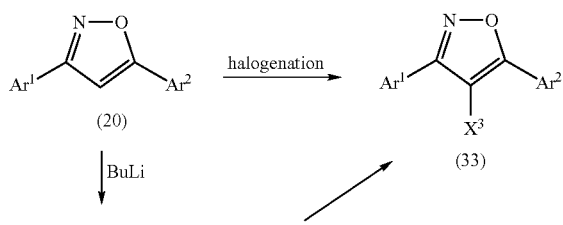

As outlined in Scheme 6, compounds of formula (20), wherein $Ar^1$ and $Ar^2$ are as defined, can be reacted with a halogenating agent, such as but not limited to Cl$_2$, Br$_2$, I$_2$, N-chlorosuccinimide, N-bromosuccinimide and SELECT-FLUOR™, to give compounds of formula (33), where $X^3$ is F, Cl, Br and I. Alternatively, compounds of formula (20) may be treated with a base, such as butyllithium, to provide an intermediate of formula (34) that can react with N-chlorosuccinimide, N-bromosuccinimide or iodine to give compounds of formula (33) as described in Stephens, C. E. et al., *J. Flu. Chem.*, 125, 1939, 2004, and Wakefield, B. J., *Science of Synthesis*, 11, 229-288, 2002.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss et al., pub. Longman Scientific & Technical, Essex CM20 2JE, England.

The compounds and processes of the present invention will be better understood in connection with the following Examples, which are intended as an illustration of and not a limitation upon the scope of the invention.

EXAMPLES

Synthesis of Arylcarbaldehyde Oximes or Heteroarylcarbaldehyde Oximes

Method OA: To a solution of aryl aldehyde or heteroaryl aldehyde (38.0 mmol) in EtOH (20 mL) and pyridine (20.0 mL) was added hydroxylamine hydrochloride (Aldrich, 3.05 g, 43.8 mmol). The mixture was stirred at ambient temperature for 12 hours. It was then concentrated to half volume, 40 mL of water was added and the mixture was stirred for additional 3 hours. The resultant white precipitate was filtered, rinsed with water (10 mL), and dried to give the corresponding arylcarbaldehyde oxime or heteroarylcarbaldehyde oxime.

Method OB: To a solution of aryl aldehyde or heteroaryl aldehyde (10.0 mmol) in EtOH (10 mL) was added hydroxylamine hydrochloride (Aldrich, 0.96 g, 15.0 mmol) and sodium acetate (Aldrich, 1.14 g, 15.0. mmol). The mixture was stirred at ambient temperature for 12 hours. Then the reaction mixture was diluted with EtOAc (100 mL) and washed with water (2×10 mL) and brine (2×10 mL). The organic solution was dried over anhydrous Na$_2$SO$_4$ for 1 hour. The drying agent was removed by filtration, and the organic solution was concentrated to give the title product.

Synthesis of N-hydroxyarylcarbimidoyl chlorides or N-hydroxyheteroarylcarbimidoyl chlorides Method C: To a solution of the corresponding arylcarbaldehyde oxime or the heteroarylcarbaldehyde oxime (20 mmol) in THF (anhydrous, Aldrich, 40 mL) was added N-chlorosuccinimide (Aldrich, 3.07 g, 23 mmol). The mixture was then heated to 60° C. for 1 hour. After cooling to ambient temperature, the reaction mixture was diluted with EtOAc (150 mL), washed with water (2×10 mL) and brine (2×20 mL), and dried over anhydrous $MgSO_4$. The drying reagent was removed by filtration. The filtrate was concentrated to give the title product.

Synthesis of Aryl Acetylenes

Method AA: Under $N_2$, ethynyltrimethylsilane (Aldrich, 0.98 g, 10 mmol), $Et_3N$ (Aldrich, 1.01 g, 10 mmol), $PdCl_2(PPh_3)_2$ (Aldrich, 70 mg, 0.1 mmol) and CuI (Aldrich, 95 mg, 0.5 mmol) were added to a solution of aryl bromide (5 mmol) in THF (20 mL). The mixture was heated to 60° C. for 12 hours. Upon cooling to ambient temperature, the reaction mixture was quenched with saturated aqueous $NH_4Cl$ solution (20 mL). The dark mixture was extracted with EtOAc (3×50 mL). The combined extracts were concentrated. The residue was dissolved in MeOH (20 mL) and stirred with KOH (1 N, 5 mL) for 2-3 hours. The mixture was concentrated, and the residue was extracted with EtOAc (3×50 mL). The combine extracts were concentrated, and the residue was purified chromatographically on silica gel [eluting solvent, EtOAc:hexanes=1:1 (v/v)] to give the titled product.

Method AB: Under $N_2$, ethynyltrimethylsilane (Aldrich, 0.98 g, 10 mmol), $Et_3N$ (Aldrich, 1.01 g, 10 mmol), $PdCl_2(PPh_3)_2$ (Aldrich, 70 mg, 0.1 mmol) and CuI (Aldrich, 95 mg, 0.5 mmol) were added to a solution of aryl iodide (5 mmol) in THF (20 mL). The mixture was stirred at ambient temperature for 12 hours and then quenched with saturated aqueous $NH_4Cl$ solution (20 mL). The dark mixture was extracted with EtOAc (3×50 mL). The combined extracts were concentrated. The residue was dissolved in MeOH (20 mL) and stirred with KOH (1 N, 5 mL) for 2-3 hours. The mixture was concentrated, and the residue was extracted with EtOAc (3×50 mL). The combined extracts were concentrated, and the residue was purified chromatographically on silica gel [eluting solvent, EtOAc:hexanes=1:1 (v/v)] to give the titled product.

Synthesis of 3,5-disubstituted-isoxazoles

Method CA: N-hydroxyarylcarbimidoyl chloride or N-hydroxyheteroarylcarbimidoyl chloride (0.5 mmol) and aryl acetylene (0.5 mmol) were combined in THF (2 mL) and stirred for 10 minutes. $Et_3N$ (Aldrich, 101 mg, 1.0 mmol) was then added. The reaction mixture was stirred at ambient temperature for 12 hours and then quenched with water (2.0 mL). The mixture was then extracted with EtOAc (2×10 mL). The combined extracts were concentrated and the residue was purified chromatographically on silica gel to provide the corresponding 3,5-disubstituted-isoxazole.

The free base can also be dissolved in EtOAc (5-10 mL) and treated with HCl (Aldrich, 4 M in dioxane, 2-3 eq.) at ambient temperature for 5-10 hours. The precipitate was collected by filtration and dried to provide the corresponding 3,5-disubstituted-isoxazole hydrochloric acid salt.

Method CB: N-hydroxyarylcarbimidoyl chloride or N-hydroxyheteroarylcarbimidoyl chloride (0.5 mmol) and aryl acetylene (0.5 mmol) were combined in THF (2 mL) and stirred for 10 minutes. $Et_3N$ (Aldrich, 101 mg, 1.0 mmol) was then added. The reaction mixture was stirred at ambient temperature for 12 hours and then quenched with water (0.5 mL). The crude material was then directly purified by preparative HPLC [Gilson System, Xbridge™ Prep C18, 5 μM, OBD™ 30×100 mm column, solvent: acetonitrile/water (pH=10 buffer), 5/95 to 95/5, flow rate of 40 mL/min]. Fractions were collected based upon UV signal threshold to provide the corresponding 3,5-disubstituted-isoxazole.

The free base can also be dissolved in EtOAc (5-10 mL) and treated with HCl (Aldrich, 4 M in dioxane, 2-3 eq.) at ambient temperature for 5-10 hours. The precipitate was collected by filtration and dried to provide the corresponding 3,5-disubstituted-isoxazole hydrochloric acid salt.

Method CD: N-hydroxyarylcarbimidoyl chloride or N-hydroxyheteroarylcarbimidoyl chloride (0.5 mmol) and aryl acetylene (0.5 mmol) were combined in THF (2 mL) and stirred for 10 minutes. $Et_3N$ (Aldrich, 101 mg, 1.0 mmol) was then added. The reaction mixture was stirred at ambient temperature for 12 hours and then quenched with water (0.5 mL). The crude material was then directly purified by preparative HPLC [Gilson System, Xbridge™ Prep C18, 5 μM, OBD™ 30×100 mm column, solvent: acetonitrile/water (0.1% v/v TFA), 5/95 to 95/5, flow rate of 40 mL/minute]. Fractions were collected based upon UV signal threshold and fractions holding the desired product were combined and concentrated under reduced pressure to provide the corresponding 3,5-disubstituted-isoxazole trifluoroacetic acid salt.

Method CC: 3-Aryl-5-halo-isoxazole or 3-heteroaryl-5-halo-isoxazole (0.5 mmol) and arylboronic acid or heteroarylboronic acid (0.75 mmol) were combined in dioxane (4 mL) and aqueous $K_2CO_3$ (2N, 1 mL). The mixture was deoxygenated and purged with nitrogen three times. $Pd(PPh_3)_4$ (Aldrich, 11.6 mg, 0.02 mmol) was then added. The reaction mixture was stirred at 70° C. for 12 hours, cooled to ambient temperature, and extracted with $CHCl_3$ (3×5 mL). The combined extracts were concentrated, and the residue was purified by preparative HPLC [Gilson System, Xbridge™ Prep C18, 5 μM, OBD™ 30×100 mm column, solvent: acetonitrile/water (pH=10 buffer), 5/95 to 95/5, flow rate of 40 mL/minute]. Fractions were collected based upon UV signal threshold to provide the corresponding 3,5-disubstituted-isoxazole.

The free base can also be dissolved in EtOAc (5-10 mL) and treated with HCl (Aldrich, 4 M in dioxane, 2-3 eq.) at ambient temperature for 5-10 hours. The precipitate was collected by filtration and dried to provide the corresponding 3,5-disubstituted-isoxazole hydrochloric acid salt.

Example 1

3,5-Di(pyridin-3-yl)isoxazole

Example 1A

N-Hydroxynicotinimidoyl chloride

The titled compound was prepared according to Method C using nicotinaldehyde oxime (Aldrich, 7.0 g, 57.3 mmol). $^1$H NMR (300 MHz, DMSO-$d_6$) δ 7.53 (dd, J=8.5, 5.4 Hz, 1H), 8.15 (dt, J=8.2, 2.0 Hz, 1H), 8.67 (dd, J=4.8, 1.6 Hz, 1H), 8.96 (d, J=2.4 Hz, 1H), 8.96 (d, J=2.4 Hz, 1H), 12.69 (s, 1H) ppm; MS (DCI/$NH_3$) m/z 159 (M+H)$^+$, 157 (M+H)$^+$.

Example 1B 3,5-Di(pyridin-3-yl)isoxazole

The titled compound was prepared as the bishydrochloride salt according to Method CA using the product of Example 1A (0.78 g, 5.0 mmol) and 3-ethynylpyridine (Aldrich, 0.52 g, 5.0 mmol). $^1$H NMR (300 MHz, DMSO-$d_6$) δ 7.76 (dd, J=8.1, 5.1 Hz, 1H), 7.79-7.86 (m, 1H), 7.98 (s, 1H), 8.44 (dt, J=8.0, 2.0, 1.9 Hz, 1H), 8.55 (dt, J=8.1, 1.9 Hz, 1H), 8.80 (dd, J=4.9, 1.5 Hz, 1H), 8.86 (dd, J=5.1, 1.7 Hz, 1H), 9.21 (d, J=2.0 Hz, 1H), 9.23 (d, J=2.0 Hz, 1H) ppm; MS (DCI/NH$_3$) m/z 224 (M+H)$^+$.

Example 2

5-(3,4-Dichlorophenyl)-3-(pyridin-3-yl)isoxazole

The titled compound was prepared as the hydrochloride salt according to Method CB using the product of Example 1A (78 mg, 0.5 mmol) and 1,2-dichloro-4-ethynylbenzene (Aldrich, 86 mg, 0.5 mmol). $^1$H NMR (300 MHz, DMSO-d$_6$) δ 7.69 (dd, J=8.1, 5.0 Hz, 1H), 7.82-8.00 (m, 3H), 8.21 (d, J=2.0 Hz, 1H), 8.38 (dt, J=7.9, 1.8 Hz, 1H), 8.78 (dd, J=4.8, 1.6 Hz, 1H), 9.14 (d, J=1.2 Hz, 1H) ppm; MS (DCI/NH$_3$) m/z 293 (M+H)$^+$, 291 (M+H)$^+$.

Example 3

5-(4-Fluoro-3-methylphenyl)-3-(pyridin-3-yl)isoxazole

The titled compound was prepared as the hydrochloride salt according to Method CB using the product of Example 1A (78 mg, 0.5 mmol) and 4-ethynyl-1-fluoro-2-methylbenzene (Aldrich, 67 mg, 0.5 mmol). $^1$H NMR (300 MHz, DMSO-d$_6$) δ 1.96 (s, 3H), 7.38 (t, J=9.6 Hz, 1H), 7.62-7.75 (m, 2H), 7.80 (ddd, J=7.9, 5.4, 2.2 Hz, 1H), 7.89 (dd, J=6.9, 1.8 Hz, 1H), 8.42 (dt, J=8.1, 1.8, 1.6 Hz, 1H), 8.79 (dd, J=5.2, 1.6 Hz, 1H), 9.16 (d, J=2.4 Hz, 1H) ppm; MS (DCI/NH$_3$) m/z 255 (M+H)$^+$.

Example 4

5-(3-Fluoro-4-(trifluoromethoxy)phenyl)-3-(pyridin-3-yl)isoxazole

The titled compound was prepared as the hydrochloride salt according to Method CB using the product of Example 1A (78 mg, 0.5 mmol) and 4-ethynyl-2-fluoro-1-(trifluoromethoxy)benzene (Apollo, 102 mg, 0.5 mmol). $^1$H NMR (300 MHz, DMSO-d$_6$) δ 7.69 (dd, J=8.0, 4.9 Hz, 1H), 7.78-7.96 (m, 3H), 8.11 (dd, J=11.0, 1.9 Hz, 1H), 8.38 (dt, J=8.1, 1.9 Hz, 1H), 8.79 (dd, J=4.9, 1.2 Hz, 1H), 9.15 (d, J=1.0 Hz, 1H) ppm; MS (DCI/NH$_3$) m/z 325 (M+H)$^+$.

Example 5

4-(3-(Pyridin-3-yl)isoxazol-5-yl)benzonitrile

The titled compound was prepared as the hydrochloride salt according to Method CB using the product of Example 1A (78 mg, 0.5 mmol) and 4-ethynylbenzonitrile (Aldrich, 64 mg, 0.6 mmol). $^1$H NMR (300 MHz, DMSO-d$_6$) δ7.69 (dd, J=8.0, 4.9 Hz, 2H), 7.96 (s, 1H), 8.03-8.20 (m, 3H), 8.39 (d, J=7.8 Hz, 1H), 8.78 (dd, J=4.7, 1.7 Hz, 1H), 9.16 (d, J=2.4 Hz, 1H) ppm; MS (DCI/NH$_3$) m/z 248 (M+H)$^+$.

Example 6

5-(4-Fluorophenyl)-3-(pyridin-3-yl)isoxazole

The titled compound was prepared as the hydrochloride salt according to Method CB using the product of Example 1A (78 mg, 0.5 mmol) and 1-ethynyl-4-fluorobenzene (Aldrich, 60 mg, 0.5 mmol). $^1$H NMR (300 MHz, DMSO-d$_6$) δ 7.40-7.52 (m, 2H), 7.70-7.81 (m, 2H), 7.92-8.08 (m, 2H), 8.44 (dt, J=8.0, 1.9 Hz, 1H), 8.80 (d, J=4.4 Hz, 1H), 9.18 (s, 1H) ppm; MS (DCI/NH$_3$) m/z 241 (M+H)$^+$.

Example 7

5-(3,5-Difluorophenyl)-3-(pyridin-3-yl)isoxazole

The titled compound was prepared as the hydrochloride salt according to Method CB using the product of Example 1A (78 mg, 0.5 mmol) and 1-ethynyl-3,5-difluorobenzene (Apollo, 69 mg, 0.5 mmol). $^1$H NMR (300 MHz, DMSO-d$_6$) δ 7.50 (tt, J=9.3, 2.4 Hz, 1H), 7.60-7.78 (m, 3H), 7.89 (s, 1H), 8.32 (dt, J=7.8, 2.2 Hz, 1H), 8.76 (d, J=3.4 Hz, 1H), 9.11 (d, J=1.7 Hz, 1H) ppm; MS (DCI/NH$_3$) m/z 259 (M+H)$^+$.

Example 8

5-(4-Bromophenyl)-3-(pyridin-3-yl)isoxazole

The titled compound was prepared as the hydrochloride salt according to Method CB using the product of Example 1A (78 mg, 0.5 mmol) and 1-bromo-4-ethynylbenzene (Alfa Aesar, 80 mg, 0.5 mmol). $^1$H NMR (300 MHz, DMSO-d$_6$) δ 7.66 (dd, J=7.7, 5.0 Hz, 1H), 7.75-8.01 (m, 5H), 8.36 (dt, J=8.0, 1.9 Hz, 1H), 8.76 (dd, J=4.8, 1.6 Hz, 1H), 9.14 (s, 1H) ppm; MS (DCI/NH$_3$) m/z 303 (M+H)$^+$, 301 (M+H)$^+$.

Example 9

3-(Pyridin-3-yl)-5-(3-(trifluoromethyl)phenyl)isoxazole

The titled compound was prepared as the hydrochloride salt according to Method CB using the product of Example 1A (78 mg, 0.5 mmol) and 1-ethynyl-3-(trifluoromethyl)benzene (Aldrich, 85 mg, 0.5 mmol). $^1$H NMR (300 MHz, DMSO-d$_6$) δ 7.64-7.76 (m, 1H), 7.81-7.96 (m, 2H), 7.98 (s, 1H), 8.20-8.30 (m, 2H), 8.41 (dt, J=8.1, 1.9 Hz, 1H), 8.79 (dd, J=4.8, 1.6 Hz, 1H), 9.17 (d, J=1.6 Hz, 1H) ppm; MS (DCI/NH$_3$) m/z 291 (M+H)$^+$.

Example 10

5-(3-Fluorophenyl)-3-(pyridin-3-yl)isoxazole

The titled compound was prepared as the hydrochloride salt according to Method CB using the product of Example 1A (78 mg, 0.5 mmol) and 1-ethynyl-3-fluorobenzene (Aldrich, 60 mg, 0.5 mmol). $^1$H NMR (300 MHz, DMSO-d$_6$) δ 7.35-7.51 (m, 1H), 7.60-7.82 (m, 4H), 7.84 (s, 1H), 8.42 (dt, J=8.1, 1.7 Hz, 1H), 8.80 (dd, J=5.0, 1.4 Hz, 1H), 9.17 (d, J=1.6 Hz, 1H) ppm; MS (DCI/NH$_3$) m/z 241 (M+H)$^+$.

Example 11

5-(4-Chlorophenyl)-3-(pyridin-3-yl)isoxazole

The titled compound was prepared as the hydrochloride salt according to Method CB using the product of Example 1A (78 mg, 0.5 mmol) and 1-chloro-4-ethynylbenzene (Aldrich, 68 mg, 0.5 mmol). $^1$H NMR (300 MHz, DMSO-d$_6$) δ 7.62-7.75 (m, 3H), 7.79 (s, 1H), 7.89-8.01 (m, 2H), 8.40 (dt, J=8.1, 1.7 Hz, 1H), 8.78 (dd, J=5.1, 1.4 Hz, 1H), 9.16 (d, J=2.0 Hz, 1H) ppm; MS (DCI/NH$_3$) m/z 259 (M+H)$^+$, 257 (M+H)$^+$.

Example 12

5-(3,5-Dimethoxyphenyl)-3-(pyridin-3-yl)isoxazole

The titled compound was prepared as the hydrochloride salt according to Method CB using the product of Example 1A (78 mg, 0.5 mmol) and 1-ethynyl-3,5-dimethoxybenzene (Aldrich, 81 mg, 0.5 mmol). $^1$H NMR (300 MHz, DMSO-$d_6$) δ 3.85 (s, 6H), 6.69 (t, J=2.2 Hz, 1H), 7.07 (d, J=2.4 Hz, 2H), 7.68 (ddd, J=8.0, 4.9, 1.0 Hz, 1H), 7.78 (s, 1H), 8.38 (dt, J=7.6, 1.9 Hz, 1H), 8.77 (dd, J=4.9, 1.5 Hz, 1H), 9.14 (d, J=1.4 Hz, 1H) ppm; MS (DCI/NH$_3$) m/z 283 (M+H)$^+$.

Example 13

3-(Pyridin-3-yl)-5-m-tolylisoxazole

The titled compound was prepared as the hydrochloride salt according to Method CB using the product of Example 1A (78 mg, 0.5 mmol) and 1-ethynyl-3-methylbenzene (Aldrich, 58 mg, 0.5 mmol). $^1$H NMR (300 MHz, DMSO-$d_6$) δ 2.42 (s, 3H), 7.37 (d, J=7.7 Hz, 1H), 7.48 (t, J=7.6 Hz, 1H), 7.67 (ddd, J=8.0, 4.9, 0.7 Hz, 1 H), 7.74-7.84 (m, 3H), 8.38 (dt, J=7.9, 2.0 Hz, 1H), 8.76 (dd, J=4.7, 1.7 Hz, 1H), 9.15 (d, J=1.7 Hz, 1H) ppm; MS (DCI/NH$_3$) m/z 237 (M+H)$^+$.

Example 14

5-(2,4-Difluorophenyl)-3-(pyridin-3-yl)isoxazole

The titled compound was prepared as the hydrochloride salt according to Method CB using the product of Example 1A (78 mg, 0.5 mmol) and 1-ethynyl-2,4-difluorobenzene (Aldrich, 69 mg, 0.5 mmol). $^1$H NMR (300 MHz, DMSO-$d_6$) δ 7.29-7.43 (m, 1H), 7.53-7.65 (m, 2H), 7.69 (dd, J=7.5, 4.7 Hz, 1H), 8.08 (td, J=8.7, 6.3 Hz, 1H), 8.48 (dt, J=7.9, 2.0 Hz, 1H), 8.78 (dd, J=4.9, 1.5 Hz, 1H), 9.23 (d, J=1.7 Hz, 1H) ppm; MS (DCI/NH$_3$) m/z 259 (M+H)$^+$.

Example 15

5-(2-Fluorophenyl)-3-(pyridin-3-yl)isoxazole

The titled compound was prepared as the hydrochloride salt according to Method CB using the product of Example 1A (78 mg, 0.5 mmol) and 1-ethynyl-2-fluorobenzene (Aldrich, 60 mg, 0.5 mmol). $^1$H NMR (300 MHz, DMSO-$d_6$) δ 7.34-7.56 (m, 2H), 7.58-7.74 (m, 3H), 8.02 (td, J=7.6, 1.7 Hz, 1H), 8.47 (dt, J=7.9, 2.0 Hz, 1H), 8.77 (dd, J=4.9, 1.5 Hz, 1H), 9.23 (d, J=2.4 Hz, 1H) ppm; MS (DCI/NH$_3$) m/z 241 (M+H)$^+$.

Example 16

5-(3,4-Difluorophenyl)-3-(pyridin-3-yl)isoxazole

The titled compound was prepared as the hydrochloride salt according to Method CB using the product of Example 1A (78 mg, 0.5 mmol) and 4-ethynyl-1,2-difluorobenzene (Apollo, 69 mg, 0.5 mmol). $^1$H NMR (300 MHz, DMSO-$d_6$) δ 7.60-7.75 (m, 2H), 7.76-7.85 (m, 2H), 8.05 (ddd, J=11.4, 7.6, 2.4 Hz, 1H), 8.37 (dt, J=7.9, 2.0 Hz, 1H), 8.78 (dd, J=5.1, 1.7 Hz, 1H), 9.14 (d, J=1.7 Hz, 1H) ppm; MS (DCI/NH$_3$) m/z 259 (M+H)$^+$.

Example 17

5-(3,4,5-Trifluorophenyl)-3-(pyridin-3-yl)isoxazole

The titled compound was prepared as the hydrochloride salt according to Method CB using the product of Example 1A (78 mg, 0.5 mmol) and 5-ethynyl-1,2,3-trifluorobenzene (Apollo, 78 mg, 0.5 mmol). $^1$H NMR (300 MHz, DMSO-$d_6$) δ 7.69 (dd, J=7.9, 4.8 Hz, 1H), 7.85 (s, 1H), 7.95 (dd, J=8.7, 6.7 Hz, 2H), 8.35 (dt, J=8.1, 1.7 Hz, 1H), 8.79 (d, J=3.6 Hz, 1H), 9.11 (s, 1H) ppm; MS (DCI/NH$_3$) m/z 277 (M+H)$^+$.

Example 18

3-(5-(Pyridin-3-yl)isoxazol-3-yl)benzonitrile

Example 18A

3-((Hydroxyimino)methyl)benzonitrile

The titled compound was prepared according to Method OA using 3-formylbenzonitrile (Aldrich). $^1$H NMR (300 MHz, DMSO-$d_6$) δ 7.62 (t, J=7.7 Hz, 1H), 7.84 (dt, J=7.8, 1.4 Hz, 1H), 7.94 (dt, J=7.8, 1.4 Hz, 1H), 7.99 (t, J=1.6 Hz, 1H), 8.21 (s, 1H), 11.58 (s, 1H) ppm; MS (DCI/NH$_3$) m/z 147 (M+H)$^+$.

Example 18B

3-Cyano-N-hydroxybenzimidoyl chloride

The titled compound was prepared according to Method C using the product of Example 18A. $^1$H NMR (300 MHz, DMSO-$d_6$) δ 7.70 (t, J=7.5 Hz, 1H), 7.94-8.02 (m, 1H), 8.07-8.19 (m, 2H), 12.75 (s, 1H) ppm; MS (DCI/NH$_3$) m/z 183 (M+H)$^+$, 181 (M+H)$^+$.

Example 18C

3-(5-(Pyridin-3-yl)isoxazol-3-yl)benzonitrile

The titled compound was prepared as the hydrochloride salt according to Method CB using the product of Example 18B (91 mg, 0.5 mmol) and 3-ethynylpyridine (Aldrich, 52 mg, 0.5 mmol). $^1$H NMR (300 MHz, DMSO-$d_6$) δ 7.64 (dd, J=7.5, 4.4 Hz, 1H), 7.80 (t, J=7.5 Hz, 1H), 7.89 (s, 1H), 8.04 (dt, J=7.7, 1.3 Hz, 1H), 8.21-8.34 (m, 2H), 8.38 (t, J=1.4 Hz, 1H), 8.74 (dd, J=4.8, 1.6 Hz, 1H), 9.13 (d, J=2.0 Hz, 1H) ppm; MS (DCI/NH$_3$) m/z 248 (M+H)$^+$.

Example 19

3-(3-(Pyridin-3-yl)isoxazol-5-yl)benzonitrile

Example 19A

3-Ethynylbenzonitrile

The titled compound was prepared according to Method AA using 3-bromobenzonitrile (Aldrich). $^1$H NMR (300 MHz, MeOH-$d_4$) δ 3.62 (s, 1H), 7.44 (t, J=7.7 Hz, 1H), 7.58-7.69 (m, 2H), 7.72 (t, J=1.4 Hz, 1H) ppm; MS (DCI/NH$_3$) m/z 128 (M+H)$^+$.

Example 19B

3-(3-(Pyridin-3-yl)isoxazol-5-yl)benzonitrile

The titled compound was prepared according to Method CB using the product of Example 1A (78 mg, 0.5 mmol) and the product of Example 19A (64 mg, 0.5 mmol). $^1$H NMR (300 MHz, MeOH-$d_4$) δ 7.53 (s, 1H), 7.61 (ddd, J=8.1, 5.0, 0.8 Hz, 1H), 7.75 (t, J=7.8 Hz, 1H), 7.88 (dt, J=7.7, 1.4 Hz, 1H), 8.23 (dt, J=8.1, 1.4 Hz, 1H), 8.31 (t, J=1.7 Hz, 1H), 8.38 (dt, J=8.1, 1.9 Hz, 1H), 8.68 (dd, J=5.1, 1.7 Hz, 1H), 9.10 (d, J=2.0 Hz, 1H) ppm; MS (DCI/NH$_3$) m/z 248 (M+H)$^+$.

Example 20

5-(3-Chlorophenyl)-3-(pyridin-3-yl)isoxazole

The titled compound was prepared according to Method CB using the product of Example 1A (78 mg, 0.5 mmol) and 1-chloro-3-ethynylbenzene (Apollo, 68 mg, 0.5 mmol). $^1$H NMR (300 MHz, MeOH-$d_4$) δ 7.46 (s, 1H), 7.49-7.55 (m, 2H), 7.60 (ddd, J=8.0, 4.9, 1.0 Hz, 1H), 7.82-7.90 (m, 1H), 7.93-8.00 (m, 1H), 8.37 (dt, J=7.9, 2.0 Hz, 1H), 8.67 (dd, J=5.1, 1.7 Hz, 1H), 9.09 (d, J=1.4 Hz, 1H) ppm; MS (DCI/NH$_3$) m/z 259 (M+H)$^+$, 257 (M+H)$^+$.

Example 21

3-(Pyridin-3-yl)-5-p-tolylisoxazole

The titled compound was prepared according to Method CB using the product of Example 1A (78 mg, 0.5 mmol) and 1-ethynyl-4-methylbenzene (Apollo, 58 mg, 0.5 mmol). $^1$H NMR (300 MHz, MeOH-$d_4$) δ 2.43 (s, 3H), 7.30 (s, 1H), 7.36 (d, J=7.8 Hz, 2H), 7.60 (dd, J=7.6, 4.6 Hz, 1H), 7.81 (d, J=8.5 Hz, 2H), 8.36 (dt, J=8.2, 1.8 Hz, 1H), 8.66 (dd, J=4.9, 1.5 Hz, 1H), 9.09 (d, J=3.1 Hz, 1H) ppm; MS (DCI/NH$_3$) m/z 237 (M+H)$^+$.

Example 22

5-Phenyl-3-(pyridin-3-yl)isoxazole

The titled compound was prepared according to Method CB using the product of Example 1A (78 mg, 0.5 mmol) and 1-ethynyl-benzene (Aldrich, 52 mg, 0.5 mmol). $^1$H NMR (300 MHz, MeOH-$d_4$) δ 7.37 (s, 1H), 7.46-7.68 (m, 4H), 7.85-8.00 (m, 2H), 8.37 (dt, J=7.9, 2.0 Hz, 1H), 8.66 (dd, J=4.9, 1.5 Hz, 1H), 9.10 (d, J=2.4 Hz, 1H) ppm; MS (DCI/NH$_3$) m/z 223 (M+H)$^+$.

Example 23

5-(2-Chlorophenyl)-3-(pyridin-3-yl)isoxazole

The titled compound was prepared according to Method CB using the product of Example 1A (78 mg, 0.5 mmol) and 1-chloro-2-ethynylbenzene (Apollo, 68 mg, 0.5 mmol). $^1$H NMR (300 MHz, MeOH-$d_4$) δ 7.43-7.56 (m, 3H), 7.56-7.70 (m, 2H), 7.98 (dd, J=5.9, 3.6 Hz, 1H), 8.39 (dt, J=7.9, 2.0 Hz, 1H), 8.67 (dd, J=4.8, 1.6 Hz, 1H), 9.12 (d, J=2.4 Hz, 1H) ppm; MS (DCI/NH$_3$) m/z 259 (M+H)$^+$, 257 (M+H)$^+$.

Example 24

5-(3-Aminophenyl)-3-(pyridin-3-yl)isoxazole

The titled compound was prepared according to Method CB using the product of Example 1A (78 mg, 0.5 mmol) and 3-ethynylaniline (Aldrich, 59 mg, 0.5 mmol). $^1$H NMR (300 MHz, MeOH-$d_4$) δ 6.83 (dt, J=7.5, 1.9 Hz, 1H), 7.10-7.33 (m, 4H), 7.59 (dd, J=8.0, 4.9 Hz, 1H), 8.35 (dt, J=8.1, 1.9 Hz, 1H), 8.65 (dd, J=4.9, 1.5 Hz, 1H), 9.08 (d, J=1.4 Hz, 1H) ppm; MS (DCI/NH$_3$) m/z 238 (M+H)$^+$.

Example 25

1-(3-(3-(Pyridin-3-yl)isoxazol-5-yl)phenyl)ethanone

The titled compound was prepared as the hydrochloride salt according to Method CB using the product of Example 1A (78 mg, 0.5 mmol) and 1-(3-ethynylphenyl)ethanone (GFS Chemicals, 72 mg, 0.5 mmol). $^1$H NMR (300 MHz, MeOH-$d_4$) δ 2.70 (s, 3H), 7.67-7.85 (m, 2H), 7.94 (s, 1H), 8.13 (dt, J=5.1, 1.5 Hz, 1H), 8.18 (dt, J=7.6, 1.5 Hz, 1H), 8.40-8.54 (m, 2H), 8.80 (dd, J=5.2, 1.6 Hz, 1H), 9.20 (d, J=1.5 Hz, 1H) ppm; MS (DCI/NH$_3$) m/z 265 (M+H)$^+$.

Example 26

3-(Pyridin-2-yl)-5-(pyridin-3-yl)isoxazole

The titled compound was prepared as the bishydrochloride salt according to Method CC using 5-iodo-3-(pyridin-2-yl)isoxazole [prepared as described by Ku, Y.-Y.; Grieme, T.; Sharma, P.; Pu, Y.-M.; Raje, P.; Morton, H.; King, S. Org. Lett. 2001, 3, 4185-4187] (136 mg, 0.5 mmol) and pyridin-3-ylboronic acid (Aldrich, 92 mg, 0.750 mmol). $^1$H NMR (300 MHz, DMSO-$d_6$) d ppm 7.52-7.64 (m, 1H), 7.75-7.83 (m, 1H), 7.86 (s, 1H), 8.03 (td, J=7.7, 1.6 Hz, 1H), 8.11 (dt, J=7.9, 1.2 Hz, 1H), 8.58 (dt, J=8.0, 1.9 Hz, 1H), 8.75-8.79 (m, 1H), 8.81 (dd, J=5.2, 1.6 Hz, 1H), 9.32 (d, J=2.4 Hz, 1H) ppm; MS (DCI/NH$_3$) m/z 224 (M+H)$^+$.

Example 27

5-(3-(pyridin-2-yl)isoxazol-5-yl)nicotinonitrile

The titled compound was prepared as the bishydrochloride salt according to Method CC using 5-iodo-3-(pyridin-2-yl)isoxazole (136 mg, 0.5 mmol) and 5-(4,4,5,5-tetramethyl-1,3,2-dioxaborolan-2-yl)nicotinonitrile (Frontier, 173 mg, 0.750 mmol). $^1$H NMR (300 MHz, DMSO-$d_6$) δ 7.60 (ddd, J=7.3, 4.8, 1.4 Hz, 1H), 7.93 (s, 1H), 8.04 (td, J=7.6, 1.8 Hz, 1H), 8.11 (dt, J=7.9, 1.2 Hz, 1H), 8.78 (ddd, J=2.9, 1.8 Hz, 1H), 8.96 (t, J=2.2 Hz, 1H), 9.16 (d, J=1.6 Hz, 1H), 9.47 (d, J=2.0 Hz, 1H) ppm; MS (DCI/NH$_3$) m/z 249 (M+H)$^+$.

Example 28

3-(5-Fluoropyridin-3-yl)-5-(pyridin-3-yl)isoxazole

Example 28A

5-Fluoronicotinaldehyde oxime

The titled compound was prepared according to Method OB using 5-fluoronicotinaldehyde (Aldrich). $^1$H NMR (300 MHz, MeOH-$d_4$) δ 7.85 (dt, J=9.5, 2.2 Hz, 1H), 8.16 (s, 1H), 8.43 (d, J=2.7 Hz, 1H), 8.57 (s, 1H) ppm; MS (DCI/NH$_3$) m/z 141 (M+H)$^+$.

Example 28B

5-Fluoro-N-hydroxynicotinimidoyl chloride

The titled compound was prepared according to Method C using the product of Example 28A. $^1$H NMR (300 MHz, MeOH-d$_4$) δ 8.01 (ddd, J=9.5, 2.7, 1.7 Hz, 1H), 8.54 (d, J=2.7 Hz, 1H), 8.86 (t, J=1.4 Hz, 1H) ppm; MS (DCI/NH$_3$) m/z 177 (M+H)$^+$, 175 (M+H)$^+$.

Example 28C 3-(5-Fluoropyridin-3-yl)-5-(pyridin-3-yl)isoxazole

The titled compound was prepared according to Method CB using the product of Example 28B (88 mg, 0.5 mmol) and 3-ethynylpyridine (Aldrich, 52 mg, 0.5 mmol). $^1$H NMR (300 MHz, MeOH-d$_4$) 87.59 (s, 1H), 7.63 (ddd, J=8.0, 5.1, 0.8 Hz, 1H), 8.19 (ddd, J=9.3, 2.8, 1.8 Hz, 1H), 8.36 (dt, J=7.9, 2.0 Hz, 1H), 8.62 (d, J=2.8 Hz, 1H), 8.68 (dd, J=5.2, 1.6 Hz, 1H), 8.99 (t, J=1.6 Hz, 1H), 9.12 (d, J=2.4 Hz, 1H) ppm; MS (DCI/NH$_3$) m/z 242 (M+H)$^+$.

Example 29

3-(3-(5-Fluoropyridin-3-yl)isoxazol-5-yl)benzonitrile

The titled compound was prepared according to Method CB using the product of Example 28B (88 mg, 0.5 mmol) and the product of Example 19A (64 mg, 0.5 mmol). $^1$H NMR (300 MHz, MeOH-d$_4$) δ 7.55 (s, 1H), 7.75 (t, J=7.9 Hz, 1H), 7.88 (dt, J=7.9, 1.4 Hz, 1H), 8.18 (ddd, J=9.3, 2.8, 1.8 Hz, 1H), 8.23 (ddd, J=7.9, 2.0, 1.2 Hz, 1H), 8.31 (t, J=1.6 Hz, 1H), 8.62 (d, J=2.8 Hz, 1H), 8.98 (t, J=1.6 Hz, 1 H) ppm; MS (DCI/NH$_3$) m/z 266 (M+H)$^+$.

Example 30

5-(3-Fluorophenyl)-3-(5-fluoropyridin-3-yl)isoxazole

The titled compound was prepared according to Method CB using the product of Example 28B (88 mg, 0.5 mmol) and 1-ethynyl-3-fluorobenzene (Aldrich, 60 mg, 0.5 mmol). $^1$H NMR (300 MHz, MeOH-d$_4$) δ 7.20-7.35 (m, 1H), 7.46 (s, 1 H), 7.58 (td, J=8.0, 5.8 Hz, 1H), 7.68 (ddd, J=9.7, 2.5, 1.7 Hz, 1H), 7.76 (dt, J=8.0, 1.1 Hz, 1H), 8.17 (ddd, J=9.4, 2.8, 1.7 Hz, 1H), 8.61 (d, J=2.7 Hz, 1H), 8.97 (t, J=1.5 Hz, 1H) ppm; MS (DCI/NH$_3$) m/z 259 (M+H)$^+$.

Example 31

5-(4-Chlorophenyl)-3-(5-fluoropyridin-3-yl)isoxazole

The titled compound was prepared according to Method CB using the product of Example 28B (88 mg, 0.5 mmol) and 1-chloro-4-ethynylbenzene (Aldrich, 68 mg, 0.5 mmol). $^1$H NMR (300 MHz, MeOH-d$_4$) δ 7.42 (s, 1H), 7.57 (dt, J=8.9, 2.3 Hz, 2H), 7.92 (dt, J=8.9, 2.3 Hz, 2H), 8.17 (ddd, J=9.3, 2.8, 1.8 Hz, 1H), 8.61 (d, J=2.8 Hz, 1H), 8.96 (t, J=1.6 Hz, 1H) ppm; MS (DCI/NH$_3$) m/z 277 (M+H)$^+$, 275 (M+H)$^+$.

Example 32

4-(3-(5-Fluoropyridin-3-yl)isoxazol-5-yl)benzonitrile

The titled compound was prepared according to Method CB using the product of Example 28B (88 mg, 0.5 mmol) and 4-ethynylbenzonitrile (Aldrich, 64 mg, 0.5 mmol). $^1$H NMR (300 MHz, MeOH-d$_4$) 87.60 (s, 1H), 7.92 (dt, J=8.6, 1.7 Hz, 2H), 8.11 (dt, J=8.6, 1.7 Hz, 2H), 8.19 (ddd, J=9.2, 2.7, 1.7 Hz, 1H), 8.62 (d, J=2.7 Hz, 1H), 8.98 (t, J=1.4 Hz, 1H) ppm; MS (DCI/NH$_3$) m/z 266 (M+H)$^+$.

Example 33

5-(4-Bromophenyl)-3-(5-fluoropyridin-3-yl)isoxazole

The titled compound was prepared according to Method CB using the product of Example 28B (88 mg, 0.5 mmol) and 1-bromo-4-ethynylbenzene (Alfa Aesar, 80 mg, 0.5 mmol). $^1$H NMR (300 MHz, MeOH-d$_4$) δ 7.43 (s, 1H), 7.72 (dt, J=8.9, 2.2 Hz, 2H), 7.85 (dt, J=8.9, 2.2 Hz, 2H), 8.17 (ddd, J=9.5, 2.7, 1.7 Hz, 1H), 8.61 (d, J=2.7 Hz, 1H), 8.96 (t, J=1.5 Hz, 1H) ppm; MS (DCI/NH$_3$) m/z 320 (M+H)$^+$, 318 (M+H)$^+$.

Example 34

5-(3,4-Dichlorophenyl)-3-(5-fluoropyridin-3-yl)isoxazole

The titled compound was prepared according to Method CB using the product of Example 28B (88 mg, 0.5 mmol) and 1,2-dichloro-4-ethynylbenzene (Aldrich, 86 mg, 0.5 mmol). $^1$H NMR (300 MHz, MeOH-d$_4$) δ 7.50 (s, 1H), 7.72 (d, J=8.3 Hz 1H), 7.86 (dd, J=8.3, 1.9 Hz 1H), 8.12 (d, J=2.0 Hz, 1H), 8.17 (ddd, J=9.1, 2.8, 1.6 Hz, 1H), 8.62 (d, J=2.8 Hz, 1H), 8.97 (t, J=1.4 Hz, 1H) ppm; MS (DCI/NH$_3$) m/z 311 (M+H)$^+$, 309 (M+H)$^+$.

Example 35

5-(3,5-Difluorophenyl)-3-(5-fluoropyridin-3-yl)isoxazole

The titled compound was prepared according to Method CB using the product of Example 28B (88 mg, 0.5 mmol) and 1-ethynyl-3,5-difluorobenzene (Apollo, 69 mg, 0.5 mmol). $^1$H NMR (300 MHz, MeOH-d$_4$) 87.16 (tt, J=9.1, 2.2 Hz, 1H), 7.53 (s, 1H), 7.54-7.63 (m, 2H), 8.17 (ddd, J=9.1, 2.8, 1.6 Hz, 1H), 8.62 (d, J=2.8 Hz, 1H), 8.97 (t, J=1.6 Hz, 1H) ppm; MS (DCI/NH$_3$) m/z 277 (M+H)$^+$.

Example 36

3-(5-Fluoropyridin-3-yl)-5-(3,4,5-trifluorophenyl)isoxazole

The titled compound was prepared according to Method CB using the product of Example 28B (88 mg, 0.5 mmol) and 5-ethynyl-1,2,3-trifluorobenzene (Apollo, 78 mg, 0.5 mmol). $^1$H NMR (300 MHz, MeOH-d$_4$) δ 7.49 (s, 1H), 7.76 (dd, J=8.3, 6.6 Hz, 2H), 0.16 (ddd, J=9.2, 2.7, 1.7 Hz, 1H), 8.62 (d, J=2.7 Hz, 1H), 8.95 (t, J=1.5 Hz, 1H) ppm; MS (DCI/NH$_3$) m/z 295 (M+H)$^+$.

Example 37

3-(5-Fluoropyridin-3-yl)-5-(4-fluorophenyl)isoxazole

The titled compound was prepared according to Method CB using the product of Example 28B (88 mg, 0.5 mmol) and 1-ethynyl-4-fluorobenzene (Aldrich, 60 mg, 0.5 mmol). $^1$H NMR (300 MHz, MeOH-d$_4$) δ 7.24-7.35 (m, 2H), 7.37 (s, 1

H), 7.92-8.02 (m, 2H), 8.17 (ddd, J=9.4, 2.8, 1.7 Hz, 1H), 8.61 (d, J=3.1 Hz, 1H), 8.96 (t, J=1.5 Hz, 1H) ppm; MS (DCI/NH$_3$) m/z 259 (M+H)$^+$.

Example 38

5-(4-Fluoro-3-methylphenyl)-3-(5-fluoropyridin-3-yl)isoxazole

The titled compound was prepared according to Method CB using the product of Example 28B (88 mg, 0.5 mmol) and 4-ethynyl-1-fluoro-2-methylbenzene (Aldrich, 67 mg, 0.5 mmol). $^1$H NMR (300 MHz, MeOH-d$_4$) δ 2.37 (d, J=2.0 Hz, 3H), 7.21 (t, J=8.9 Hz, 1H), 7.33 (s, 1H), 7.73-7.80 (m, 1H), 7.83 (dd, J=6.6, 1.9 Hz, 1H), 8.16 (ddd, J=9.2, 2.7, 1.7 Hz, 1H), 8.60 (d, J=2.7 Hz, 1H), 8.96 (t, J=1.5 Hz, 1 H) ppm; MS (DCI/NH$_3$) m/z 273 (M+H)$^+$.

Example 39

3-(5-Fluoropyridin-3-yl)-5-(3-(trifluoromethyl)phenyl)isoxazole

The titled compound was prepared according to Method CB using the product of Example 28B (88 mg, 0.5 mmol) and 1-ethynyl-3-(trifluoromethyl)benzene (Aldrich, 85 mg, 0.5 mmol). $^1$H NMR (300 MHz, MeOH-d$_4$) δ 7.57 (s, 1H), 7.71-7.96 (m, 2H), 8.09-8.32 (m, 3H), 8.62 (d, J=2.7 Hz, 1H), 8.98 (t, J=1.5 Hz, 1H) ppm; MS (DCI/NH$_3$) m/z 309 (M+H)$^+$.

Example 40

3-(5-Fluoropyridin-3-yl)-5-(3-methylphenyl)isoxazole

The titled compound was prepared according to Method CB using the product of Example 28B (88 mg, 0.5 mmol) and 1-ethynyl-3-methylbenzene (Aldrich, 58 mg, 0.5 mmol). $^1$H NMR (300 MHz, MeOH-d$_4$) δ 2.44 (s, 3H), 7.29-7.38 (m, 2 H), 7.42 (t, J=7.6 Hz, 1H), 7.64-7.81 (m, 2H), 8.17 (ddd, J=9.4, 2.8, 1.7 Hz, 1H), 8.60 (d, J=2.7 Hz, 1H), 8.97 (t, J=1.7 Hz, 1H) ppm; MS (DCI/NH$_3$) m/z 255 (M+H)$^+$.

Example 41

5-(3-Fluoro-4-(trifluoromethoxy)phenyl)-3-(5-fluoropyridin-3-yl)isoxazole

The titled compound was prepared according to Method CB using the product of Example 28B (88 mg, 0.5 mmol) and 4-ethynyl-2-fluoro-1-(trifluoromethoxy)benzene (Apollo, 102 mg, 0.5 mmol). $^1$H NMR (300 MHz, MeOH-d$_4$) δ 7.51 (s, 1H), 7.59-7.69 (m, 1H), 7.85 (ddd, J=8.8, 2.0, 1.4 Hz, 1H), 7.93 (dd, J=10.9, 2.0 Hz, 1H), 8.17 (ddd, J=9.2, 2.7, 1.7 Hz, 1H), 8.62 (d, J=2.7 Hz, 1H), 8.97 (t, J=1.5 Hz, 1H) ppm; MS (DCI/NH$_3$) m/z 343 (M+H)$^+$.

Example 42

3-(3-(5-Fluoropyridin-3-yl)isoxazol-5-yl)aniline

The titled compound was prepared as the trifluoroacetic acid salt according to Method CD using the product of Example 28B (88 mg, 0.5 mmol) and 3-ethynylaniline (Aldrich, 59 mg, 0.5 mmol). $^1$H NMR (300 MHz, MeOH-d$_4$) δ 6.82-6.91 (m, 1H), 7.13-7.49 (m, 4H), 8.16 (dt, J=9.2, 2.2 Hz, 1H), 8.60 (d, J=2.7 Hz, 1 H), 8.96 (s, 1H) ppm; MS (DCI/NH$_3$) m/z 256 (M+H)$^+$.

Example 43

5-(2-Chlorophenyl)-3-(5-fluoropyridin-3-yl)isoxazole

The titled compound was prepared according to Method CB using the product of Example 28B (88 mg, 0.5 mmol) and 1-chloro-2-ethynylbenzene (Apollo, 68 mg, 0.5 mmol). $^1$H NMR (300 MHz, MeOH-d$_4$) δ 7.48-7.54 (m, 2H), 7.56 (s, 1H), 7.59-7.68 (m, 1H), 7.97 (dd, J=5.9, 3.9 Hz, 1H), 8.21 (ddd, J=9.2, 2.7, 1.7 Hz, 1H), 8.61 (d, J=2.7 Hz, 1H), 9.00 (t, J=1.5 Hz, 1H) ppm; MS (DCI/NH$_3$) m/z 277 (M+H)$^+$, 275 (M+H)$^+$.

Example 44

5-(Pyridin-3-yl)-3-(pyrimidin-5-yl)isoxazole

Example 44A

Pyrimidine-5-carbaldehyde oxime

The titled compound was prepared according to Method OB using pyrimidine-5-carbaldehyde (Aldrich). $^1$H NMR (300 MHz, DMSO-d$_6$) δ8.22 (s, 1.0; H), 8.99 (s, 2H), 11.83 (s, 0.8H), 11.95 (s, 0.2H) ppm; MS (DCI/NH$_3$) m/z 124 (M+H)$^+$.

Example 44B

N-Hydroxypyrimidine-5-carbimidoyl chloride

The titled compound was prepared according to Method C using the product of Example 44A. $^1$H NMR (300 MHz, MeOH-d$_4$) δ 9.14 (s, 2H), 9.29 (s, 1H) ppm; MS (DCI/NH$_3$) m/z 160 (M+H)$^+$, 158 (M+H)$^+$.

Example 44C 5-(pyridin-3-yl)-3-(pyrimidin-5-yl)isoxazole

The titled compound was prepared as the bishydrochloride salt according to Method CB using the product of Example 44B (79 mg, 0.5 mmol) and 3-ethynylpyridine (Aldrich, 52 mg, 0.5 mmol). $^1$H NMR (300 MHz, DMSO-d$_6$) δ 7.70 (ddd, J=8.1, 4.9, 0.8 Hz, 1H), 7.96 (s, 1H), 8.37 (ddd, J=8.2, 1.9, 1.7 Hz, 1H), 8.77 (dd, J=4.7, 1.7 Hz, 1H), 9.17 (dd, J=2.2, 0.8 Hz, 1H), 9.34 (s, 2H), 9.36 (s, 1H) ppm; MS (DCI/NH$_3$) m/z 225 (M+H)$^+$.

Example 45

3-(3-(Pyrimidin-5-yl)isoxazol-5-yl)benzonitrile

The titled compound was prepared as the hydrochloride salt according to Method CB using the product of Example 44B (79 mg, 0.5 mmol) and the product of Example 19A (64 mg, 0.5 mmol). $^1$H NMR (300 MHz, DMSO-d$_6$) δ 7.83 (t, J=7.8 Hz, 1H), 7.94 (s, 1H), 8.04 (dt, J=7.8, 1.4 Hz, 1H), 8.25 (dt, J=8.1, 1.4 Hz, 1H), 8.42 (t, J=1.5 Hz, 1H), 9.32 (s, 2H), 9.36 (s, 1H) ppm; MS (DCI/NH$_3$) m/z 249 (M+H)$^+$.

Example 46

5-(2,4-Difluorophenyl)-3-(pyrimidin-5-yl)isoxazole

The titled compound was prepared as the hydrochloride salt according to Method CB using the product of Example 44B (79 mg, 0.5 mmol) and 1-ethynyl-2,4-difluorobenzene (Aldrich, 69 mg, 0.5 mmol). $^1$H NMR (300 MHz, DMSO-$d_6$) δ 7.30-7.42 (m, 1H), 7.61 (ddd, J=11.5, 9.1, 2.4 Hz, 1H), 7.68 (d, J=3.2 Hz, 1H), 8.08 (td, J=8.6, 6.5 Hz, 1H), 9.35 (s, 1H), 9.39 (s, 2H) ppm; MS (DCI/NH$_3$) m/z 260 (M+H)$^+$.

Example 47

3-(Pyrimidin-5-yl)-5-(3,4,5-trifluorophenyl)isoxazole

The titled compound was prepared as the hydrochloride salt according to Method CB using the product of Example 44B (79 mg, 0.5 mmol) and 5-ethynyl-1,2,3-trifluorobenzene (Apollo, 78 mg, 0.5 mmol). $^1$H NMR (300 MHz, DMSO-$d_6$) δ 7.88 (s, 1H), 7.95 (dd, J=8.6, 6.6 Hz, 2H), 9.29 (s, 2H), 9.36 (s, 1H) ppm; MS (DCI/NH$_3$) m/z 278 (M+H)$^+$.

Example 48

4-(3-(Pyrimidin-5-yl)isoxazol-5-yl)benzonitrile

The titled compound was prepared as the hydrochloride salt according to Method CB using the product of Example 44B (79 mg, 0.5 mmol) and 4-ethynylbenzonitrile (Aldrich, 64 mg, 0.5 mmol). $^1$H NMR (300 MHz, DMSO-$d_6$) δ 7.99 (s, 1H), 8.10 (s, 4H), 9.34 (s, 2H), 9.36 (s, 1H) ppm; MS (DCI/NH$_3$) m/z 249 (M+H)$^+$.

Example 49

5-(3,5-Difluorophenyl)-3-(pyrimidin-5-yl)isoxazole

The titled compound was prepared as the hydrochloride salt according to Method CB using the product of Example 44B (79 mg, 0.5 mmol) and 1-ethynyl-3,5-difluorobenzene (Apollo, 69 mg, 0.5 mmol). $^1$H NMR (300 MHz, DMSO-$d_6$) δ 7.52 (tt, J=9.5, 2.4 Hz, 1H), 7.62-7.78 (m, 2H), 7.93 (s, 1H), 9.30 (s, 2H), 9.36 (s, 1H) ppm; MS (DCI/NH$_3$) m/z 260 (M+H)$^+$.

Example 50

5-(3-Fluorophenyl)-3-(pyrimidin-5-yl)isoxazole

The titled compound was prepared as the hydrochloride salt according to Method CB using the product of Example 44B (79 mg, 0.5 mmol) and 1-ethynyl-3-fluorobenzene (Aldrich, 60 mg, 0.5 mmol). $^1$H NMR (300 MHz, DMSO-$d_6$) δ 7.35-7.51 (m, 1H), 7.67 (td, J=8.1, 5.9 Hz, 1H), 7.73-7.82 (m, 2H), 7.86 (s, 1H), 9.32 (s, 2H), 9.36 (s, 1H) ppm; MS (DCI/NH$_3$) m/z 242 (M+H)$^+$.

Example 51

5-(4-Bromophenyl)-3-(pyrimidin-5-yl)isoxazole

The titled compound was prepared as the hydrochloride salt according to Method CB using the product of Example 44B (79 mg, 0.5 mmol) and 1-bromo-4-ethynylbenzene (Alfa Aesar, 80 mg, 0.5 mmol). $^1$H NMR (300 MHz, DMSO-$d_6$) δ 7.77-7.95 (m, 5H), 9.32 (s, 2H), 9.35 (s, 1H) ppm; MS (DCI/NH$_3$) m/z 304 (M+H)$^+$, 302 (M+H)$^+$.

Example 52

5-Phenyl-3-(pyrimidin-5-yl)isoxazole

The titled compound was prepared as the hydrochloride salt according to Method CB using the product of Example 44B (79 mg, 0.5 mmol) and 1-ethynyl-benzene (Aldrich, 52 mg, 0.5 mmol). $^1$H NMR (300 MHz, DMSO-$d_6$) δ 7.47-7.70 (m, 3H), 7.78 (s, 1H), 7.87-7.98 (m, 2H), 9.34 (s, 2H), 9.35 (s, 1H) ppm; MS (DCI/NH$_3$) m/z 224 (M+H)$^+$.

Example 53

5-(4-Chlorophenyl)-3-(pyrimidin-5-yl)isoxazole

The titled compound was prepared as the hydrochloride salt according to Method CB using the product of Example 44B (79 mg, 0.5 mmol) and 1-chloro-4-ethynylbenzene (Aldrich, 68 mg, 0.5 mmol). $^1$H NMR (300 MHz, DMSO-$d_6$) δ 7.69 (dt, J=9.0, 2.3, Hz, 2H), 7.82 (s, 1H), 7.94 (dt, J=9.0, 2.4 Hz, 2H), 9.32 (s, 2H), 9.35 (s, 1H) ppm; MS (DCI/NH$_3$) m/z 260 (M+H)$^+$, 258 (M+H)$^+$.

Example 54

5-(3,4-Difluorophenyl)-3-(pyrimidin-5-yl)isoxazole

The titled compound was prepared as the hydrochloride salt according to Method CB using the product of Example 44B (79 mg, 0.5 mmol) and 4-ethynyl-1,2-difluorobenzene (Apollo, 69 mg, 0.5 mmol). $^1$H NMR (300 MHz, DMSO-$d_6$) δ 7.71 (ddd, J=10.5, 8.3, 8.3 Hz, 1H), 7.77-7.86 (m, 2H), 8.04 (ddd, J=11.4, 7.6, 2.0 Hz, 1 H), 9.31 (s, 2H), 9.35 (s, 1H) ppm; MS (DCI/NH$_3$) m/z 260 (M+H)$^+$.

Example 55

3-(Pyrimidin-5-yl)-5-p-tolylisoxazole

The titled compound was prepared as the hydrochloride salt according to Method CB using the product of Example 44B (79 mg, 0.5 mmol) and 1-ethynyl-4-methylbenzene (Apollo, 58 mg, 0.5 mmol). $^1$H NMR (300 MHz, DMSO-$d_6$) δ 2.40 (s, 3H), 7.42 (d, J=8.1 Hz, 2H), 7.70 (s, 1H), 7.81 (d, J=8.5 Hz, 2H), 9.32 (s, 2H), 9.34 (s, 1H) ppm; MS (DCI/NH$_3$) m/z 238 (M+H)$^+$.

Example 56

5-(3,4-Dichlorophenyl)-3-(pyrimidin-5-yl)isoxazole

The titled compound was prepared as the hydrochloride salt according to Method CB using the product of Example 44B (79 mg, 0.5 mmol) and 1,2-dichloro-4-ethynylbenzene (Aldrich, 86 mg, 0.5 mmol). $^1$H NMR (300 MHz, DMSO-$d_6$) δ 7.86-7.96 (m, 3H), 8.20 (d, J=1.7 Hz, 1H), 9.31 (s, 2H), 9.36 (s, 1H) ppm; MS (DCI/NH$_3$) m/z 294 (M+H)$^+$, 292 (M+H)$^+$.

Example 57

5-(3-(Difluoromethoxy)phenyl)-3-(pyrimidin-5-yl)isoxazole

The titled compound was prepared as the hydrochloride salt according to Method CB using the product of Example 44B (79 mg, 0.5 mmol) and 1-(difluoromethoxy)-3-ethynyl-benzene (Fluorochemicals, 84 mg, 0.5 mmol). $^1$H NMR (300 MHz, DMSO-$d_6$) δ 7.33-7.46 (m, 2H), 7.56-7.74 (m, 2H), 7.81 (dt, J=7.9, 1.1 Hz, 1H), 7.87 (s, 1H), 9.33 (s, 2H), 9.35 (s, 1H) ppm; MS (DCI/NH$_3$) m/z 290 (M+H)$^+$.

Example 58

5-(4-Fluorophenyl)-3-(pyrimidin-5-yl)isoxazole

The titled compound was prepared as the hydrochloride salt according to Method CB using the product of Example 44B (79 mg, 0.5 mmol) and 1-ethynyl-4-fluorobenzene (Aldrich, 60 mg, 0.5 mmol). $^1$H NMR (300 MHz, DMSO-$d_6$) δ 7.40-7.57 (m, 2H), 7.76 (s, 1H), 7.90-8.06 (m, 2H), 9.32 (s, 2H), 9.35 (s, 1H) ppm; MS (DCI/NH$_3$) m/z 242 (M+H)$^+$.

Example 59

3-(Pyrimidin-5-yl)-5-m-tolylisoxazole

The titled compound was prepared as the hydrochloride salt according to Method CB using the product of Example 44B (79 mg, 0.5 mmol) and 1-ethynyl-3-methylbenzene (Aldrich, 58 mg, 0.5 mmol). $^1$H NMR (300 MHz, DMSO-$d_6$) δ 2.42 (s, 3H), 7.39 (d, J=7.8 Hz, 1H), 7.49 (t, J=7.8 Hz, 1H), 7.67-7.79 (m, 3H), 9.33 (s, 2 H), 9.35 (s, 1H) ppm; MS (DCI/NH$_3$) m/z 238 (M+H)$^+$.

Example 60

4-(3-(5-Fluoropyridin-3-yl)isoxazol-5-yl)phthalonitrile

Example 60A

4-Ethynylphthalonitrile

The titled compound was prepared according to Method AB using 4-iodophthalonitrile (Aldrich). $^1$H NMR (300 MHz, MeOH-$d_4$) δ 4.10 (s, 1H), 7.87-7.99 (m, 2H), 8.07 (d, J=1.0 Hz, 1H) ppm; MS (DCI/NH$_3$) m/z 170 (M+NH$_4$)$^+$.

Example 60B 4-(3-(5-Fluoropyridin-3-yl)isoxazol-5-yl)phthalonitrile

The titled compound was prepared according to Method CB using the product of product of Example 28B (88 mg, 0.5 mmol) and product of Example 60A (76 mg, 0.5 mmol). $^1$H NMR (300 MHz, MeOH-$d_4$) 87.71 (s, 1H), 8.15 (d, J=8.8 Hz, 1H), 8.19 (ddd, J=9.2, 2.7, 1.7 Hz, 1H), 8.37 (dd, J=8.2, 2.7 Hz, 1H), 8.55 (d, J=1.4 Hz, 1H), 8.63 (d, J=2.7 Hz, 1H), 8.98 (t, J=1.5 Hz, 1H) ppm; MS (DCI/NH$_3$) m/z 291 (M+H)$^+$.

Example 61

3-(5-Fluoropyridin-3-yl)-5-phenylisoxazole

The titled compound was prepared according to Method CB using the product of product of Example 28B (88 mg, 0.5 mmol) and 1-ethynylbenzene (Aldrich, 52 mg, 0.5 mmol). $^1$H NMR (300 MHz, MeOH-$d_4$) δ 7.39 (s, 1H), 7.49-7.60 (m, 3H), 7.88-7.97 (m, 2H), 8.17 (ddd, J=9.3, 2.9, 1.7 Hz, 1H), 8.60 (d, J=2.7 Hz, 1H), 8.97 (t, J=1.4 Hz, 1H) ppm; MS (DCI/NH$_3$) m/z 241 (M+H)$^+$.

Example 62

5-(2-Chlorophenyl)-3-(5-fluoropyridin-3-yl)isoxazole

The titled compound was prepared according to Method CB using the product of product of Example 28B (88 mg, 0.5 mmol) and 1-chloro-2-ethynylbenzene (Apollo, 68 mg, 0.5 mmol). $^1$H NMR (300 MHz, MeOH-$d_4$) δ 7.43-7.55 (m, 2H), 7.56 (s, 1H), 7.60-7.71 (m, 1H), 7.93-8.05 (m, 1H), 8.21 (ddd, J=9.3, 2.9, 1.7 Hz, 1H), 8.61 (d, J=2.7 Hz, 1H), 9.00 (t, J=1.5 Hz, 1H) ppm; MS (DCI/NH$_3$) m/z 275 (M+H)$^+$, 277 (M+H)$^+$.

Example 63

1-(3-(3-(5-Fluoropyridin-3-yl)isoxazol-5-yl)phenyl)ethanone

The titled compound was prepared according to Method CB using the product of product of Example 28B (88 mg, 0.5 mmol) and 1-(3-ethynylphenyl)ethanone (GFS Chemicals, 72 mg, 0.5 mmol). $^1$H NMR (300 MHz, MeOH-$d_4$) δ 2.69 (s, 3H), 7.54 (s, 1H), 7.71 (t, J=7.5 Hz, 1H), 8.08-8.24 (m, 3H), 8.51 (t, J=1.8 Hz, 1H), 8.62 (d, J=2.8 Hz, 1H), 8.99 (t, J=1.6 Hz, 1H) ppm; MS (DCI/NH$_3$) m/z 283 (M+H)$^+$.

Example 64

5-(3-(Difluoromethoxy)phenyl)-3-(5-fluoropyridin-3-yl)isoxazole

The titled compound was prepared according to Method CB using the product of product of Example 28B (88 mg, 0.5 mmol) and 1-(difluoromethoxy)-3-ethynylbenzene (Fluorochemicals, 84 mg, 0.5 mmol). $^1$H NMR (300 MHz, MeOH-$d_4$) δ 6.95 (s, 1H), 7.31 (dd, J=8.3, 2.0 Hz, 1H), 7.47 (s, 1H), 7.59 (t, J=8.1 Hz, 1H), 7.70 (t, J=2.1 Hz, 1H), 7.77-7.83 (m, 1H), 8.18 (ddd, J=9.3, 2.8, 1.8 Hz, 1H), 8.61 (d, J=2.8 Hz, 1H), 8.98 (t, J=1.4 Hz, 1H) ppm; MS (DCI/NH$_3$) m/z 307 (M+H)$^+$.

Example 65

5-(3,5-Dimethoxyphenyl)-3-(5-fluoropyridin-3-yl)isoxazole

The titled compound was prepared according to Method CB using the product of product of Example 28B (88 mg, 0.5 mmol) and 1-ethynyl-3,5-dimethoxybenzene (Aldrich, 81 mg, 0.5 mmol). $^1$H NMR (300 MHz, MeOH-$d_4$) 83.87 (s, 6H), 6.64 (t, J=2.2 Hz, 1H), 7.06 (d, J=2.4 Hz, 2H), 7.40 (s, 1H), 8.16 (ddd, J=9.2, 2.7, 1.7 Hz, 1H), 8.60 (d, J=2.7 Hz, 1H), 8.96 (t, J=1.5 Hz, 1H) ppm; MS (DCI/NH$_3$) m/z 301 (M+H)$^+$.

Example 66

3-Chloro-5-(3-(5-fluoropyridin-3-yl)isoxazol-5-yl)benzonitrile

Example 66A

3-Chloro-5-ethynylbenzonitrile

The titled compound was prepared according to Method AA using 3-bromo-5-chlorobenzonitrile (Biofine). $^1$H NMR (300 MHz, MeOH-d$_4$) δ3.86 (s, 1H), 7.77-7.81 (m, 2H), 7.81-7.85 (m, 1H) ppm; MS (DCI/NH$_3$) m/z 162 (M+H)$^+$, 164 (M+H)$^+$.

Example 66B

3-Chloro-5-(3-(5-fluoropyridin-3-yl)isoxazol-5-yl)benzonitrile

The titled compound was prepared according to Method CB using the product of Example 28B (88 mg, 0.5 mmol) and the product of Example 66A (82 mg, 0.5 mmol). $^1$H NMR (300 MHz, MeOH-d$_4$) δ 8.00 (s, 1H), 8.22 (ddd, J=9.5, 2.7, 1.7 Hz, 1H), 8.26 (dd, J=2.0, 1.4 Hz, 1H), 8.33 (t, J=1.7 Hz, 1H), 8.40 (t, J=1.5 Hz, 1H), 8.79 (d, J=2.7 Hz, 1H), 8.98 (t, J=1.7 Hz, 1H) ppm; MS (DCI/NH$_3$) m/z 300 (M+H)$^+$, 302 (M+H)$^+$.

Example 67

3-Chloro-5-(3-(pyridin-3-yl)isoxazol-5-yl)benzonitrile

The titled compound was prepared according to Method CB using the product of Example 1A (78 mg, 0.5 mmol) and the product of Example 66A (82 mg, 0.5 mmol). $^1$H NMR (300 MHz, MeOH-d$_4$) δ 7.62 (ddd, J=8.0, 4.9, 0.7 Hz, 1H), 7.97 (s, 1H), 8.24 (dd, J=2.0, 1.4 Hz, 1H), 8.28 (dt, J=8.1, 1.9 Hz, 1H), 8.34 (t, J=1.7 Hz, 1H), 8.41 (t, J=1.4 Hz, 1H), 8.75 (dd, J=4.7, 1.7 Hz, 1H), 9.09 (d, J=1.4 Hz, 1H) ppm; MS (DCI/NH$_3$) m/z 282 (M+H)$^+$, 284 (M+H)$^+$.

Example 68

2-Fluoro-5-(3-(pyridin-3-yl)isoxazol-5-yl)benzonitrile

Example 68A

5-Ethynyl-2-fluorobenzonitrile

The titled compound was prepared according to Method AB using 2-fluoro-5-iodobenzonitrile (Apollo). $^1$H NMR (300 MHz, MeOH-d$_4$) δ 3.70 (s, 1H), 7.37 (t, J=8.9 Hz, 1H), 7.80 (ddd, J=8.8, 5.1, 2.0 Hz, 5H), 7.88 (dd, J=6.1, 2.2 Hz, 1H) ppm; MS (DCI/NH$_3$) m/z 146 (M+H)$^+$.

Example 68B

2-Fluoro-5-(3-(pyridin-3-yl)isoxazol-5-yl)benzonitrile

The titled compound was prepared according to Method CB using the product of Example 1A (78 mg, 0.5 mmol) and the product of Example 68A (73 mg, 0.5 mmol). $^1$H NMR (300 MHz, MeOH-d$_4$) δ 7.49 (s, 1H), 7.52-7.68 (m, 2H), 8.28 (ddd, J=8.8, 5.1, 2.4 Hz, 1H), 8.33-8.41 (m, 2H), 8.68 (dd, J=4.9, 1.5 Hz, 1H), 9.09 (d, J=2.4 Hz, 1H) ppm; MS (DCI/NH$_3$) m/z 266 (M+H)$^+$.

Example 69

3-(5-Chloropyridin-3-yl)-5-(pyridin-3-yl)isoxazole

Example 69A

5-Chloronicotinaldehyde oxime

The titled compound was prepared according to Method OB using 5-chloronicotinaldehyde (Adesis). $^1$H NMR (300 MHz, DMSO-d$_6$) δ 8.07 (t, J=2.0 Hz, 1H), 8.21 (s, 1H), 8.62 (d, J=2.4 Hz, 1H), 8.73 (d, J=1.7 Hz, 1H), 11.75 (s, 1H) ppm; MS (DCI/NH$_3$) m/z 157 (M+H)$^+$, 159 (M+H)$^+$.

Example 69B

5-Chloro-N-hydroxynicotinimidoyl chloride

The titled compound was prepared according to Method C using the product of Example 69A. $^1$H NMR (300 MHz, DMSO-d$_6$) δ 8.20 (t, J=2.2 Hz, 1H), 8.75 (d, J=2.4 Hz, 1H), 8.91 (d, J=2.0 Hz, 1H), 12.90 (s, 1H) ppm; MS (DCI/NH$_3$) m/z 191 (M+H)$^+$, 193 (M+H)$^+$.

Example 69C 3-(5-Chloropyridin-3-yl)-5-(pyridin-3-yl)isoxazole

The titled compound was prepared according to Method CB using the product of Example 69B (57 mg, 0.3 mmol) and 3-ethynylpyridine (Aldrich, 31.0 mg, 0.3 mmol). $^1$H NMR (300 MHz, DMSO-d$_6$) δ 7.65 (ddd, J=7.9, 4.8, 0.8 Hz, 1H), 7.92 (s, 1H), 8.30 (dt, J=7.7, 2.2, 2.0 Hz, 1H), 8.45 (t, J=2.2 Hz, 1H), 8.75 (dd, J=4.8, 1.6 Hz, 1H), 8.82 (d, J=2.4 Hz, 1H), 9.09 (d, J=2.0 Hz, 1H), 9.13 (dd, J=2.4, 0.8 Hz, 1H) ppm; MS (DCI/NH$_3$) m/z 260 (M+H)$^+$, 258 (M+H)$^+$.

Example 70

3-(5-Chloropyridin-3-yl)-5-(3,4-dichlorophenyl)isoxazole

The titled compound was prepared according to Method CB using the product of Example 69B (57 mg, 0.3 mmol) and 1,2-dichloro-4-ethynylbenzene (Aldrich, 51 mg, 0.3 mmol). $^1$H NMR (300 MHz, DMSO-d$_6$) δ 7.89 (d, J=1.2 Hz, 2H), 7.93 (s, 1H), 8.18 (s, 1H), 8.40-8.44 (m, 1H), 8.82 (d, J=2.4 Hz, 1H), 9.06 (d, J=2.0 Hz, 1H) ppm; MS (DCI/NH$_3$) m/z 325 (M+H)$^+$, 327 (M+H)$^+$, 329 (M+H)$^+$.

Example 71

3-(5-Chloropyridin-3-yl)-5-(2,4-difluorophenyl)isoxazole

The titled compound was prepared according to Method CB using the product of Example 69B (57 mg, 0.3 mmol) and 1-ethynyl-2,4-difluorobenzene (Aldrich, 41 mg, 0.3 mmol). $^1$H NMR (300 MHz, DMSO-d$_6$) δ 7.30-7.43 (m, 1H), 7.61 (ddd, J=11.4, 9.2, 2.8 Hz, 1H), 7.68 (d, J=3.2 Hz, 1H), 8.07 (td, J=8.5, 6.3 Hz, 1H), 8.54 (t, J=2.0 Hz, 1H), 8.80 (d, J=2.4 Hz, 1H), 9.15 (d, J=2.0 Hz, 1H) ppm; MS (DCI/NH$_3$) m/z 293 (M+H)$^+$, 295 (M+H)$^+$.

Example 72

5-(4-Chlorophenyl)-3-(5-chloropyridin-3-yl)isoxazole

The titled compound was prepared according to Method CB using the product of Example 69B (57 mg, 0.3 mmol) and 1-chloro-4-ethynylbenzene (Aldrich, 41 mg, 0.3 mmol). $^1$H NMR (300 MHz, DMSO-d$_6$) δ7.69 (dt, J=8.9, 2.6, 2.4 Hz, 2H), 7.82 (s, 1H), 7.93 (dt, J=8.9, 2.4, 2.2 Hz, 2H), 8.44 (t, J=2.2 Hz, 1H), 8.81 (d, J=2.4 Hz, 1H), 9.08 (d, J=1.6 Hz, 1H) ppm; MS (DCI/NH$_3$) m/z 291 (M+H)$^+$, 293 (M+H)$^+$.

Example 73

4-(3-(5-Chloropyridin-3-yl)isoxazol-5-yl)benzonitrile

The titled compound was prepared according to Method CB using the product of Example 69B (57 mg, 0.3 mmol) and 4-ethynylbenzonitrile (Aldrich, 38 mg, 0.3 mmol). $^1$H NMR (300 MHz, DMSO-$d_6$) δ8.00 (s, 1H), 8.09 (s, 4H), 8.45 (t, J=2.1 Hz, 1H), 8.82 (d, J=2.4 Hz, 1H), 9.09 (d, J=1.6 Hz, 1H) ppm; MS (DCI/NH$_3$) m/z 282 (M+H)$^+$, 284 (M+H)$^+$.

Example 74

3-(5-Chloropyridin-3-yl)-5-(3,5-difluorophenyl)isoxazole

The titled compound was prepared according to Method CB using the product of Example 69B (57 mg, 0.3 mmol) and 1-ethynyl-3,5-difluorobenzene (Apollo, 41 mg, 0.3 mmol). $^1$H NMR (300 MHz, DMSO-$d_6$) δ 7.51 (tt, J=9.3, 2.4 Hz, 1 H), 7.61-7.74 (m, 2H), 7.93 (s, 1H), 8.41 (t, J=2.1 Hz, 1H), 8.82 (d, J=2.4 Hz, 1 H), 9.06 (d, J=1.7 Hz, 1H) ppm; MS (DCI/NH$_3$) m/z 293 (M+H)$^+$, 295 (M+H)$^+$.

Example 75

3-(5-Chloropyridin-3-yl)-5-(3,4,5-trifluorophenyl)isoxazole

The titled compound was prepared according to Method CB using the product of Example 69B (57 mg, 0.3 mmol) and 5-ethynyl-1,2,3-trifluorobenzene (Apollo, 47 mg, 0.3 mmol). $^1$H NMR (300 MHz, DMSO-$d_6$) δ 7.87 (s, 1H), 7.92 (dd, J=8.6, 6.6 Hz, 2H), 8.39 (t, J=2.0 Hz, 1H), 8.82 (d, J=2.4 Hz, 1H), 9.04 (d, J=1.7 Hz, 1H) ppm; MS (DCI/NH$_3$) m/z 311 (M+H)$^+$, 313 (M+H)$^+$.

Example 76

3-(5-Chloropyridin-3-yl)-5-p-tolylisoxazole

The titled compound was prepared according to Method CB using the product of Example 69B (57 mg, 0.3 mmol) and 1-ethynyl-4-methylbenzene (Apollo, 35 mg, 0.3 mmol). $^1$H NMR (300 MHz, DMSO-$d_6$) δ 2.40 (s, 3H), 7.41 (d, J=8.1 Hz, 2 H), 7.71 (s, 1H), 7.80 (d, J=8.1 Hz, 2H), 8.43 (dd, J=2.4, 1.7 Hz, 1H), 8.80 (d, J=2.4 Hz, 1H), 9.08 (d, J=2.0 Hz, 1H) ppm; MS (DCI/NH$_3$) m/z 271 (M+H)$^+$, 273 (M+H)$^+$.

Example 77

3-(5-Chloropyridin-3-yl)-5-(3,4-difluorophenyl)isoxazole

The titled compound was prepared according to Method CB using the product of Example 69B (57 mg, 0.3 mmol) and 4-ethynyl-1,2-difluorobenzene (Apollo, 41 mg, 0.3 mmol). $^1$H NMR (300 MHz, DMSO-$d_6$) δ 7.63-7.81 (m, 2H), 7.82 (s, 1H), 8.02 (ddd, J=11.4, 7.6, 2.0 Hz, 1H), 8.41 (t, J=2.0 Hz, 1H), 8.81 (d, J=2.4 Hz, 1H), 9.06 (d, J=2.0 Hz, 1H) ppm; MS (DCI/NH$_3$) m/z 291 (M+H)$^+$, 293 (M+H)$^+$.

Example 78

3-(5-Chloropyridin-3-yl)-5-(4-fluorophenyl)isoxazole

The titled compound was prepared according to Method CB using the product of Example 69B (57 mg, 0.3 mmol) and 1-ethynyl-4-fluorobenzene (Aldrich, 36 mg, 0.3 mmol). $^1$H NMR (300 MHz, DMSO-$d_6$) δ 7.41-7.57 (m, 2H), 7.76 (s, 1H), 7.90-8.05 (m, 2H), 8.43 (t, J=2.2 Hz, 1H), 8.80 (d, J=2.4 Hz, 1H), 9.08 (d, J=1.6 Hz, 1H) ppm; MS (DCI/NH$_3$) m/z 275 (M+H)$^+$, 277 (M+H)$^+$.

Example 79

5-(3-Chlorophenyl)-3-(5-chloropyridin-3-yl)isoxazole

The titled compound was prepared according to Method CB using the product of Example 69B (57 mg, 0.3 mmol) and 1-chloro-3-ethynylbenzene (Apollo, 41 mg, 0.3 mmol). $^1$H NMR (300 MHz, DMSO-$d_6$) δ 7.61-7.68 (m, 2H), 7.85-7.89 (m, 1H), 7.90 (s, 1H), 7.96-8.00 (m, 1H), 8.43 (t, J=2.1 Hz, 1H), 8.81 (d, J=2.4 Hz, 1H), 9.08 (d, J=1.6 Hz, 1H) ppm; MS (DCI/NH$_3$) m/z 291 (M+H)$^+$, 293 (M+H)$^+$.

Example 80

3-(5-Chloropyridin-3-yl)-5-phenylisoxazole

The titled compound was prepared according to Method CB using the product of Example 69B (57 mg, 0.3 mmol) and 1-ethynyl-benzene (Aldrich, 31 mg, 0.3 mmol). $^1$H NMR (300 MHz, DMSO-$d_6$) δ 7.52-7.66 (m, 3H), 7.78 (s, 1H), 7.85-7.98 (m, 2H), 8.45 (t, J=2.1 Hz, 1H), 8.80 (d, J=2.4 Hz, 1H), 9.09 (d, J=1.7 Hz, 1H) ppm; MS (DCI/NH$_3$) m/z 257 (M+H)$^+$, 259 (M+H)$^+$.

Example 81

3-(5-Chloropyridin-3-yl)-5-m-tolylisoxazole

The titled compound was prepared according to Method CB using the product of Example 69B (57 mg, 0.3 mmol) and 1-ethynyl-3-methylbenzene (Aldrich, 35 mg, 0.3 mmol). $^1$H NMR (300 MHz, DMSO-$d_6$) δ 2.42 (s, 3H), 7.38 (d, J=7.5 Hz, 1H), 7.49 (t, J=7.6 Hz, 1H), 7.66-7.75 (m, 2H), 7.75 (s, 1H), 8.44 (t, J=2.1 Hz, 1 H), 8.80 (d, J=2.4 Hz, 1H), 9.09 (d, J=2.0 Hz, 1H) ppm; MS (DCI/NH$_3$) m/z 271 (M+H)$^+$, 273 (M+H)$^+$.

Example 82

3-(5-Chloropyridin-3-yl)-5-(4-fluoro-3-methylphenyl)isoxazole

The titled compound was prepared according to Method CB using the product of Example 69B (57 mg, 0.3 mmol) and 4-ethynyl-1-fluoro-2-methylbenzene (Aldrich, 40 mg, 0.3 mmol). $^1$H NMR (300 MHz, DMSO-$d_6$) δ2.34 (d, J=2.0 Hz, 3H), 7.38 (t, J=9.2 Hz, 1H), 7.72 (s, 1H), 7.74-7.81 (m, 1H), 7.84-7.91 (m, 1H), 8.42 (t, J=2.1 Hz, 1H), 8.80 (d, J=2.4 Hz, 1H), 9.07 (d, J=1.7 Hz, 1H) ppm; MS (DCI/NH$_3$) m/z 289 (M+H)$^+$, 291 (M+H)$^+$.

Example 83

3-(Pyrazin-2-yl)-5-(pyridin-3-yl)isoxazole

Example 83A

Methyl pyrazine-2-carboxylate

A solution of pyrazine-2-carboxylic acid (Aldrich, 12.41 g, 0.1 mol) in MeOH (Aldrich, anhydrous, 100 mL) was stirred with H₂SO₄ (Aldrich, concentrated, 2 mL) at reflux for 6 hours. The reaction mixture was then concentrated and treated with saturated aqueous Na₂CO₃ solution (20 mL) till pH=8-9. The mixture was extracted with EtOAc (3×100 mL), and the combined extracts were washed with brine (2×20 mL) and dried over MgSO₄. The drying agent was removed by filtration. The organic solution was concentrated and dried to give the title compound ¹H NMR (300 MHz, CDCl₃) δ 4.06 (s, 3H), 8.73 (dd, J=2.4, 1.6 Hz, 1H), 8.79 (d, J=2.4 Hz, 1H), 9.33 (d, J=1.6 Hz, 1H) ppm. MS (DCI/NH₃) m/z 139 (M+H)⁺.

Example 83B

Pyrazine-2-carbaldehyde

A solution of the product of Example 83A (6.91 g, 50 mmol) in THF (Aldrich, anhydrous, 150 mL) was cooled down to −78° C. and a solution of LiAlH₄ (Aldrich, 1.898 g, 50.0 mmol) in THF (50 mL) was added slowly via an additional funnel. The mixture was stirred at −78° C. under N₂ for 1 hour, and then it was then carefully and slowly quenched with HOAc (Aldrich, 10 mL) at −70° C. The mixture was slowly warmed up to ambient temperature and stirred for 10 hours. After being concentrated, the residue was stirred with HCl (2 N, 15 mL) in CH₂Cl₂ (300 mL) for 20 minutes and then filtered through diatomaceous earth to remove solid inorganic salt. The organic filtrate solution was concentrated and the residue was dissolved in EtOAc (100 mL) and filtered through diatomaceous earth again. The organic filtrate solution was concentrated to give the titled compound. ¹H NMR (300 MHz, DMSO-d₆) δ 8.91 (dd, 1H), 8.94 (d, 1H), 9.12 (d, J=1.6 Hz, 1H), 10.08 (s, 1H) ppm; MS (DCI/NH₃) m/z 109 (M+H)⁺.

Example 83C

Pyrazine-2-carbaldehyde oxime

The titled compound was prepared according to Method OB using the product of Example 83B. ¹H NMR (300 MHz, DMSO-d₆) δ 8.15 (s, 1H), 8.58-8.70 (m, 2H), 9.00 (d, J=1.4 Hz, 1H), 12.03 (s, 1H) ppm; MS (DCI/NH₃) m/z 124 (M+H)⁺.

Example 83D

N-Hydroxypyrazine-2-carbimidoyl chloride

The titled compound was prepared according to Method C using the product of Example 83C. ¹H NMR (300 MHz, DMSO-d₆) δ 8.71-8.79 (m, 2H), 9.10 (d, J=1.7 Hz, 1H), 13.04 (s, 1H) ppm; MS (DCI/NH₃) m/z 158 (M+H)⁺, 160 (M+H)⁺.

Example 83E 3-(Pyrazin-2-yl)-5-(pyridin-3-yl)isoxazole

The titled compound was prepared as the bishydrochloride salt according to Method CB using the product of Example 83D (79 mg, 0.5 mmol) and 3-ethynylpyridine (Aldrich, 0.52 mg, 0.5 mmol). ¹H NMR (300 MHz, DMSO-d₆) δ 7.77 (dd, J=7.9, 5.2 Hz, 1H), 7.92 (s, 1H), 8.55 (dt, J=7.9, 1.8 Hz, 2H), 8.76-8.98 (m, 3 H), 9.32 (d, J=1.2 Hz, 2H) ppm; MS (DCI/NH₃) m/z 225 (M+H)⁺.

Example 84

3-Chloro-5-(3-(pyrazin-2-yl)isoxazol-5-yl)benzonitrile

The titled compound was prepared according to Method CB using the product of Example 83D (79 mg, 0.5 mmol) and the product of Example 66A (82 mg, 0.5 mmol). ¹H NMR (300 MHz, DMSO-d₆) δ7.66 (s, 1H), 7.97 (t, J=1.6 Hz, 1H), 8.30 (d, J=1.6 Hz, 2H), 8.71 (d, J=2.4 Hz, 1H), 8.77 (dd, J=2.8, 1.6 Hz, 1H), 9.31 (d, J=1.6 Hz, 1H) ppm; MS (DCI/NH₃) m/z 283 (M+H)⁺, 285 (M+H)⁺.

Example 85

2-Fluoro-5-(3-(pyrazin-2-yl)isoxazol-5-yl)benzonitrile

The titled compound was prepared according to Method CB using the product of Example 83D (79 mg, 0.5 mmol) and the product of Example 68A (73 mg, 0.5 mmol). ¹H NMR (300 MHz, MeOH-d₄) 57.57 (t, J=8.9 Hz, 1H), 7.55 (s, 1H), 8.30 (ddd, J=8.9, 5.0, 2.4 Hz, 1H), 8.40 (dd, J=5.9, 2.0 Hz, 1H), 8.71 (d, J=2.8 Hz, 1H), 8.74-8.80 (m, 1H), 9.30 (d, J=1.6 Hz, 1H) ppm; MS (DCI/NH₃) m/z 267 (M+H)⁺.

Example 86

3-(3-(Pyrazin-2-yl)isoxazol-5-yl)benzonitrile

The titled compound was prepared according to Method CB using the product of Example 83D (79 mg, 0.5 mmol) and the product of Example 19A (64 mg, 0.5 mmol). ¹H NMR (300 MHz, MeOH-d₄) δ 7.59 (s, 1H), 7.75 (t, J=8.1 Hz, 1H), 7.88 (dt, J=8.0, 1.4, 1.2 Hz, 1H), 8.21-8.30 (m, 1H), 8.31-8.37 (m, 1H), 8.71 (d, J=2.7 Hz, 1H), 8.77 (dd, J=2.5, 1.5 Hz, 1H), 9.31 (d, J=1.7 Hz, 1H) ppm; MS (DCI/NH₃) m/z 249 (M+H)⁺.

Example 87

5-(3-Chlorophenyl)-3-(pyrazin-2-yl)isoxazole

The titled compound was prepared according to Method CB using the product of Example 83D (79 mg, 0.5 mmol) and 1-chloro-3-ethynylbenzene (Apollo, 68 mg, 0.5 mmol). ¹H NMR (300 MHz, MeOH-d₄) δ7.49 (s, 1H), 7.51-7.59 (m, 2 H), 7.85-7.91 (m, 1H), 7.94-8.04 (m, 1H), 8.70 (d, J=2.4 Hz, 1H), 8.76 (dd, J=2.5, 1.5 Hz, 1H), 9.30 (d, J=1.7 Hz, 1H) ppm; MS (DCI/NH₃) m/z 258 (M+H)⁺, 260 (M+H)⁺.

Example 88

4-(3-(Pyrazin-2-yl)isoxazol-5-yl)benzonitrile

The titled compound was prepared according to Method CB using the product of Example 83D (79 mg, 0.5 mmol) and 4-ethynylbenzonitrile (Aldrich, 64 mg, 0.5 mmol). ¹H NMR (300 MHz, MeOH-d₄) δ 7.62 (s, 1H), 7.92 (dt, J=8.5, 1.7 Hz, 2H), 8.13 (dt, J=8.5, 1.7 Hz, 2H), 8.71 (d, J=2.4 Hz, 1H), 8.77 (dd, J=2.6, 1.4 Hz, 1 H), 9.31 (d, J=1.6 Hz, 1H) ppm; MS (DCI/NH₃) m/z 249 (M+H)⁺.

Example 89

5-Phenyl-3-(pyrazin-2-yl)isoxazole

The titled compound was prepared according to Method CB using the product of Example 83D (79 mg, 0.5 mmol) and 1-ethynyl-benzene (Aldrich, 52 mg, 0.5 mmol). $^1$H NMR (300 MHz, MeOH-d$_4$) δ 7.41 (s, 1H), 7.47-7.70 (m, 3H), 7.86-8.08 (m, 2H), 8.70 (d, J=2.4 Hz, 1H), 8.76 (dd, J=2.8, 1.6 Hz, 1H), 9.29 (d, J=1.2 Hz, 1H) ppm; MS (DCI/NH$_3$) m/z 224 (M+H)$^+$.

Example 90

5-(3-Fluorophenyl)-3-(pyrazin-2-yl)isoxazole

The titled compound was prepared according to Method CB using the product of Example 83D (79 mg, 0.5 mmol) and 1-ethynyl-3-fluorobenzene (Aldrich, 60 mg, 0.5 mmol). $^1$H NMR (300 MHz, MeOH-d$_4$) δ 7.19-7.33 (m, 1H), 7.48 (s, 1 H), 7.58 (td, J=8.1, 5.8 Hz, 1H), 7.69 (dt, J=9.6, 2.2 Hz, 1H), 7.77 (dt, J=8.0, 1.1 Hz, 1H), 8.70 (d, J=2.4 Hz, 1H), 8.76 (dd, J=2.4, 1.7 Hz, 1H), 9.29 (d, J=1.4 Hz, 1H) ppm; MS (DCI/NH$_3$) m/z 242 (M+H)$^+$.

Example 91

5-(4-Fluorophenyl)-3-(pyrazin-2-yl)isoxazole

The titled compound was prepared according to Method CB using the product of Example 83D (79 mg, 0.5 mmol) and 1-ethynyl-4-fluorobenzene (Aldrich, 60 mg, 0.5 mmol). $^1$H NMR (300 MHz, MeOH-d$_4$) δ 5.70-5.81 (m, 2H), 5.85 (s, 1 H), 6.35-6.55 (m, 2H), 7.15 (d, J=2.4 Hz, 1H), 7.19-7.26 (m, 1H), 7.75 (d, J=1.6 Hz, 1H) ppm; MS (DCI/NH$_3$) m/z 242 (M+H)$^+$.

Example 92

5-(3,4-Difluorophenyl)-3-(pyrazin-2-yl)isoxazole

The titled compound was prepared according to Method CB using the product of Example 83D (79 mg, 0.5 mmol) and 4-ethynyl-1,2-difluorobenzene (Apollo, 69 mg, 0.5 mmol). $^1$H NMR (300 MHz, MeOH-d$_4$) δ 7.38-7.54 (m, 2H), 7.74-7.84 (m, 1H), 7.90 (ddd, J=11.1, 7.5, 2.0 Hz, 1H), 8.70 (d, J=2.4 Hz, 1H), 8.76 (dd, J=2.4, 1.6 Hz, 1H), 9.29 (d, J=1.6 Hz, 1H) ppm; MS (DCI/NH$_3$) m/z 260 (M+H)$^+$.

Example 93

3-(Pyrazin-2-yl)-5-(3,4,5-trifluorophenyl)isoxazole

The titled compound was prepared according to Method CB using the product of Example 83D (79 mg, 0.5 mmol) and 5-ethynyl-1,2,3-trifluorobenzene (Apollo, 78 mg, 0.5 mmol). $^1$H NMR (300 MHz, MeOH-d$_4$) δ 7.53 (s, 1H), 7.79 (dd, J=8.5, 6.4 Hz, 2H), 8.70 (d, J=2.4 Hz, 1H), 8.76 (dd, J=2.5, 1.5 Hz, 1H), 9.29 (d, J=1.7 Hz, 1H) ppm; MS (DCI/NH$_3$) m/z 278 (M+H)$^+$.

Example 94

1-(3-(3-(Pyrazin-2-yl)isoxazol-5-yl)phenyl)ethanone

The titled compound was prepared according to Method CB using the product of Example 83D (79 mg, 0.5 mmol) and 1-(3-ethynylphenyl)ethanone (GFS Chemicals, 72 mg, 0.5 mmol). $^1$H NMR (300 MHz, MeOH-d$_4$) δ 2.70 (s, 3H), 7.55 (s, 1H), 7.71 (t, J=7.8 Hz, 1H), 8.07-8.23 (m, 2H), 8.52 (t, J=1.7 Hz, 1H), 8.70 (d, J=2.7 Hz, 1H), 8.74-8.82 (m, 1H), 9.31 (d, J=1.7 Hz, 1H) ppm; MS (DCI/NH$_3$) m/z 266 (M+H)$^+$.

Example 95

3-(6-Chloropyridin-3-yl)-5-(2,4-difluorophenyl)isoxazole

Example 95A

6-Chloronicotinaldehyde oxime

The titled compound was prepared according to Method OB using 6-chloronicotinaldehyde (Aldrich). $^1$H NMR (300 MHz, MeOH-d$_4$) δ 7.46 (d, J=8.1 Hz, 1 H), 8.05 (dd, J=8.0, 2.5 Hz, 1H), 8.12 (s, 1H), 8.51 (d, J=2.4 Hz, 1H) ppm; MS (DCI/NH$_3$) m/z 157 (M+H)$^+$, 159 (M+H)$^+$.

Example 95B

6-Chloro-N-hydroxynicotinimidoyl chloride

The titled compound was prepared according to Method C using the product of Example 95A. $^1$H NMR (300 MHz, MeOH-d$_4$) δ 7.52 (d, J=8.5 Hz, 1H), 8.20 (dd, J=8.5, 2.7 Hz, 1H), 8.78 (d, J=1.7 Hz, 1H) ppm; MS (DCI/NH$_3$) m/z 190 (M+H)$^+$, 192 (M+H)$^+$.

Example 95C 3-(6-Chloropyridin-3-yl)-5-(2,4-difluorophenyl)isoxazole

The titled compound was prepared according to Method CB using the product of Example 95B (79 mg, 0.5 mmol) and 1-ethynyl-2,4-difluorobenzene (Aldrich, 68 mg, 0.5 mmol). $^1$H NMR (300 MHz, CDCl$_3$) δ 6.93-7.14 (m, 3H), 7.47 (d, J=7.5 Hz, 1H), 8.02 (td, J=8.6, 6.3 Hz, 1H), 8.18 (dd, J=8.1, 2.7 Hz, 1H), 8.86 (dd, J=2.5, 0.8 Hz, 1H) ppm; MS (DCI/NH$_3$) m/z 293 (M+H)$^+$, 295 (M+H)$^+$.

Example 96

5-(3-Chlorophenyl)-3-(6-chloropyridin-3-yl)isoxazole

The titled compound was prepared according to Method CB using the product of Example 95B (79 mg, 0.5 mmol) and 1-chloro-3-ethynylbenzene (Apollo, 68 mg, 0.5 mmol). $^1$H NMR (300 MHz, CDCl$_3$) δ 6.88 (s, 1H), 7.43-7.52 (m, 3H), 7.69-7.78 (m, 1H), 7.81-7.89 (m, 1H), 8.18 (dd, J=8.3, 2.4 Hz, 1H), 8.84 (d, J=2.8 Hz, 1H) ppm; MS (DCI/NH$_3$) m/z 291 (M+H)$^+$, 293 (M+H)$^+$.

Compositions of the Invention

Another embodiment of the invention provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers.

Another embodiment of the invention provides pharmaceutical compositions, comprising:
(i) a nicotinic receptor ligand,
(ii) an α4β2 PAM, and
(iii) at least one pharmaceutically acceptable carrier or excipient.

Another embodiment of the invention provides pharmaceutical compositions, comprising:
(i) a nicotinic receptor ligand,
(ii) the compound of formula (I), and (iii) at least one pharmaceutically acceptable carrier or excipient.

The pharmaceutical compositions can be formulated for oral administration in solid or liquid form, for parenteral injection or for rectal administration.

The pharmaceutical compositions of this embodiment of the invention can be administered to humans and other mammals orally, rectally, parenterally, intracisternally, intravaginally, intraperitoneally, topically (as by powders, ointments or drops), buccally or as an oral or nasal spray.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringers solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vagina and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids.

Methods of Use

The biological effects of the compounds of the invention result from positive allosteric modulation of an α4β2 subtype of nicotinic acetylcholine receptor. Representative compounds of the invention, represented by Examples 1-96, demonstrate α4β2 NNR PAM activity. As such, compounds and compositions of the invention are useful for the treatment of conditions and disorders related to cholinergic dysfunction and for conditions and disorders responsive to the action of NNR modulators. The method is useful for treating, preventing or both treating and preventing conditions and disorders related to α4β2 NNR PAM activity, particularly in mammals.

More particularly, the method is useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's disease, dementia associated with Lewy bodies, dementia associated with Down's syndrome, schizophrenia, smoking cessation, substance abuse including alcohol abuse, amyotrophic lateral sclerosis, Huntington's disease, diminished CNS function associated with traumatic brain injury, acute pain, post-surgical pain, chronic pain, inflammatory pain, and neuropathic pain. The method is useful for conditions and disorders characterized by neuropsychological and cognitive dysfunction, for example in Alzheimer's disease, bipolar disorder, schizophrenia, schizoaffective disorder, and other related disorders characterized by neuropsychological and cognitive dysfunction, in particular.

Compounds of the invention also are useful for treating, preventing or both treating and preventing pain, particularly in mammals. Administration of compounds of the invention is useful for treating nociceptive and neuropathic forms of pain, for example, chronic pain, analgesic pain, post-surgical pain, neuropathic pain, and diabetic neuropathy. Such compounds are particularly beneficial for reducing adverse ganglionic effects such as at gastrointestinal systems (e.g. emesis) and for enhancing the effects of NNR ligands in such treatment.

A further aspect of the invention relates to a method of selectively modulating NNR activity, for example α4β2 NNR PAM activity, in combination with a nicotinic agonist or partial agonist to improve the tolerability of therapy using such nicotinic agonist or partial agonist, which is further described herein below. When dosed in combination with NNR agonists, such compounds could enhance efficacy in various disease states including pain and cognitive deficits by preferentially modulating α4β2 activity, and enabling improved separation from potential adverse emesis, cardiovascular and other effects.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in a pharmaceutically acceptable salt. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or animal ranges from about 0.10 mg/kg body weight to about 500 mg/kg body weight. More preferable doses can be in the range of from about 0.10 mg/kg body weight to about 50 mg/kg body weight. If desired, the effective daily dose can be divided into multiple doses for purposes of administration. Consequently, single dose compositions may contain such amounts or submultiples thereof to make up the daily dose. When co-administered with other nicotinic ligands (agonist, partial agonists), the dose ranges of the compounds of this invention may be adjusted to achieve desirable efficacy and tolerability profiles.

Use with Neuronal Nicotinic Acetylcholine Receptor Ligands

It has been found that the efficacy of nicotinic receptor ligands known in the art can be improved by combining the nicotinic receptor ligand, particularly an α4β2 receptor ligand (agonist, partial agonist), with compounds of the invention, i.e. a nicotinic acetylcholine receptor α4β2 subtype selective PAM. Such combinations are highly efficient for improving the efficacy of α4β2 ligand for treatment of pain and other disease indications such as cognitive deficits when compared to administration of an α4β2 receptor ligand alone.

Nicotinic acetylcholine ligands modulate the function by altering the activity of the receptor. Suitable compounds also can be partial agonists that partially block or partially activate the α4β2 receptor or agonists that activate the receptor. PAMs are compounds that potentiate receptor responses to acetylcholine without themselves triggering receptor activation or desensitization, or either, of the receptor. Nicotinic acetylcholine receptor α4β2 receptor ligands suitable for the invention can include full agonists or partial agonists, and can exhibit varying degrees of selectivity towards the α4β2 receptor.

One manner for characterizing interactions with α4β2 receptor is by assessing $K_i$ values for the displacement of [$^3$H]-cytisine binding. Typical ligands can have $K_i$ values ranging from 1 µM to 10 µM. The [$^3$H]-cytisine binding assays have been well reported; however, further details for carrying out the assays can be obtained in International Publication No. WO 99/32480; U.S. Pat. Nos. 5,948,793 and 5,914,328; WO 2004/018607; U.S. Pat. No. 6,809,105; WO 00/71534; and U.S. Pat. No. 6,833,370.

Accordingly, α4β2 receptor ligands suitable for the invention can be compounds of various chemical classes. Particularly, some examples of α4β2 receptor ligands suitable for the invention include, but are not limited to, heterocyclic ethers, N-substituted diazabicycles, and heterocyclic substituted amino azacycles (see International Publication No. WO 99/32480, published Jul. 1, 1999; U.S. Pat. No. 5,948,793, issued Sep. 7, 1999; U.S. Pat. No. 5,914,328, issued Jun. 22, 1999; International Publication No. WO 2004/0186107, published Sep. 23, 2004; U.S. Pat. No. 6,809,105, issued Oct. 26, 2004; International Publication No. WO 00/71534, published Nov. 30, 2000; U.S. Pat. No. 6,833,370, issued Dec. 21, 2004; all of which are hereby incorporated by reference in their entirety). Further description and methods for preparing the compounds have been reported in patents, patent publications, and international patent publications cited.

Various forms of pain, psychiatric and neurological disorders can be treated by concurrently administering to a patient (i.e. a human) in need thereof, an α4β2 PAM and an α4β2 receptor ligand. Such combination may be especially useful in expanding the dosage range for obtaining therapeutically beneficial effects.

Establishing such a proper dosing schedule will be readily apparent to one skilled in the art, such as a physician treating various pain states.

The dosage range at which the α4β2 PAM and an α4β2 receptor ligand will be administered concurrently can vary widely. The specific dosage will be chosen by the patient's physician taking into account the particular compounds chosen, the severity of the patient's illness, any other medical conditions or diseases the patient is suffering from, other drugs the patient is taking and their potential to cause an interaction or adverse event, the patient's previous response to medication, and other factors.

The α4β2 PAM and an α4β2 receptor ligand should be administered concurrently in amounts that are effective to treat the patient's pain, cognitive disorder, or related condition. In more general terms, one would create a combination of the present invention by choosing a dosage of an α4β2 PAM and an α4β2 receptor ligand according to the spirit of the guidelines presented above.

In another embodiment of the invention, the method is carried out by administering an α4β2 PAM together with an α4β2 receptor ligand in any manner which provides effective levels of the compounds in the body at the same time.

In another embodiment of the invention, the method is carried out by administering an α4β2 PAM selected from Examples 1-96 described herein, together with an α4β2 receptor ligand in any manner which provides effective levels of the compounds in the body at the same time.

Various embodiments of the invention can be administered to humans and other mammals orally, rectally, parenterally, intracisternally, intravaginally, intraperitoneally, topically (as by powders, ointments or drops), bucally or as an oral or nasal spray. Various embodiments of the invention should be construed to cover any route of administration that is appropriate for the medications involved and for the patient. For example, transdermal administration may be very desirable for patients who are forgetful or petulant about taking oral medicine. Injections may be appropriate for patients refusing their medication. One of the drugs may be administered by one route, such as oral, and the others may be administered by the transdermal, percutaneous, intravenous, intramuscular, intranasal, intrarectal or intravaginal route, in particular circumstances. The route of administration may be varied in any way, limited by the physical properties of the drugs and the convenience of the patient and the caregiver.

Combination Use in Pain Therapy

Based on the diversity of the mechanisms underlying chronic pain (e.g. nociceptive or neuropathic, degrees of pain intensity, various etiologies etc), currently available pain medications are not efficacious in all patients or in all pain conditions. Analgesics can be broadly categorized as non-opioid analgesics (acetaminophen and non-steroidal anti-inflammatory drugs (NSAIDs)), opioid analgesics (morphine) and adjuvant analgesics or co-analgesics (antiepileptic drugs and antidepressants). In a simplified classification, non-opioid analgesics are mostly used to relieve mild to moderate nociceptive pain, adjuvant analgesics (gabapentin, pregabalin) are used to relieve neuropathic pain, and opioid analgesics are used to treat severe pain of all origins, depending on the dose prescribed.

NNR ligands act at multiple locations throughout the pain pathway to relieve pain. NNRs are found on primary sensory neurons (periphery) where nociceptive information is initiated, in the cell body regions of these neurons (i.e. the dorsal root ganglion or DRG), the dorsal spinal cord where the first pain synapse is located, in the brainstem cell body regions that control descending innervation, as well as in the higher brain regions that integrate and perceive sensory information such as the thalamus and the cortex. The current theory supported by evidence from multiple sources (reviewed in Decker et al., Curr. Topics Med. Chem., 4: 369, 2004) is that anti-nociceptive effects of NNR ligands are mediated by activation of brain stem nuclei with descending inhibitory inputs to the spinal cord. Additional pathways may also mediate analgesic effects of NNR agonists in persistent or neuropathic pain.

One other aspect of the invention is the potential to enhance efficacy of other medications used for treating pain. As noted above, examples of currently used drugs include opioids, gabapentin, pregabalin, duloxetine and others. Novel mechanisms such as cannabinoids, vanilloid receptor antagonists and sodium channel blockers are also being developed for the treatment of pain. For many of these mechanisms, it is emerging that a component of efficacy may be driven by activation of descending inhibitory inputs. For example, opioid analgesics can block pain transmission, in part by increasing descending inhibitory pathways to modulate pain transmission at the spinal level (Pasternack, G. W., *Clin. Neuropharmacol.* 16: 1, 1993; Lauretti, G. T., *Expert Reviews in Neurotherapeutics*, 6: 613-622, 2006). Since these drugs exert their effect via activating descending inhibitory inputs, and these pathways can be shared or commonly activated by α4β2 NNR ligands, it is anticipated that co-administration of compounds of the invention, as α4β2 selective PAMs, can lead to enhanced efficacy of other analgesic agents by amplifying the descending inhibitory control of spinal cord activation. Thus, combining compounds of the invention with such therapeutic agents for pain affords the opportunity to create analgesic medications with either a broader or superior spectrum of efficacy that would improve the treatment of chronic pain.

Accordingly, another embodiment of the invention is a method for use in treating or preventing pain, including neuropathic pain and cognitive disorders in a patient in need thereof, comprising:
  (i) administering an amount of neuronal nicotinic receptor ligand to the patient; and
  (ii) administering an amount of the compound of formula I to the patient, wherein the amounts of (i) and (ii) together are more effective in treating pain or cognitive disorders.

Another embodiment of the invention is a method for use in treating or preventing pain in a patient in need thereof, comprising:
  (i) administering an amount of the compound of formula I to the patient; and
  (ii) administering a pain medication comprising a compound selected from an opioid, gabapentin, pregabalin, duloxetine, a cannabinoid ligand, a vanilloid receptor antagonist, and a sodium channel blocker wherein a descending modulatory pathway that is shared or commonly activated via the α4β2 nicotinic receptor mechanism is activated.

Determination of Biological Activity

One manner to characterize α4β2 PAM activity is by characterization in clonal cell lines (for example, human embryonic kidney 293 cells) expressing the human neuronal nicotinic acetylcholine receptor subtype α4β2, particularly by use of Fluorescent Image Plate Reader technology. Effects on calcium flux or membrane potential changes can be assessed. Such assays have been reported and further details for carrying out the assays can be obtained in International Publication No. WO 2006/114400. Another method to identify and characterize allosteric modulator activity is by expressing the α4β2 subunits in *Xenopus* oocytes, and by measuring electrophysiological effects on ligand-evoked current responses as previously described in Curtis, L., et al., *Molecular Pharmacology*, 61: 127-135, 2002.

To determine the effectiveness of representative compounds of this invention as ligands for α4β2 PAM activity, the compounds of the invention can be evaluated according to the Calcium Flux Assay described below.

Calcium Flux Assays using Cells Expressing NNR Subtypes

Human embryonic kidney (HEK) 293 cells stably expressing human α4β2 or α3β4 combinations are grown to confluency in 162 cm$^2$ tissue culture flasks in DMEM media supplemented with 10% FBS and 25 μg/ml zeocin and 200 μg/ml hygromycin B. Cells expressing rat or ferret subunits may also be used. For assessing α3* or α7* selectivity, IMR-32 cells may also be used. IMR-32 neuroblastoma cells (ATCC) are grown to confluency in 162 cm$^2$ tissue culture flasks in minimum essential media supplemented with 10% FBS and 1 mM sodium pyruvate, 1% non-essential amino acids and 1% antibiotic-antimycotic. For the calcium flux assay, c cells are then dissociated using cell dissociation buffer and 100-150 μl per well of 3.5×10$^5$ cells/ml cell suspension (~50,000-100,000 cells/well) was plated into 96-well black plates (poly-D-lysine precoated) with clear bottom and maintained for 24-48 hours in a tissue culture incubator at 37° C. under an atmosphere of 5% $CO_2$: 95% air. Other clonal cell lines or primary cell cultures that express endogenous α4* nicotinic receptors may also be used in this assay. Calcium flux was measured using calcium-3 assay kit (Molecular Devices, Sunnyvale, Calif.) or fluo-4 (Invitrogen). A stock solution of the dye was prepared by dissolving each vial supplied by the vendor in Hank's balanced salt solution buffer (HBSS) or 150 mM NMDG, 20 mM $CaCl_2$ containing 10 mM HEPES. The stock solution was diluted 1:20 using the same buffer before use. The growth media was removed from the cells. The cells were loaded with 100 μl of the dye per well and incubated at room temperature for up to one hour for HEK 293 clonal stable cell lines or 30 minutes-45 minutes at 37° C. for IMR-32 cells. Fluorescence measurements were read simultaneously from all the wells by a Fluorometic Imaging Plate Reader (FLIPR) at an excitation wavelength of 480 nm and an emission wavelength of 520 nm. Baseline fluorescence was measured for the first 6 seconds at which 3× concentrations of modulator/test compounds were added to the cell plate at 50 μl and incubated for five minutes. The fluorescence intensity was captured every second for the first 1 minute followed by every 5 seconds for an additional 4 minutes. This procedure was followed by 50 μl of 4× concentration of agonist and readings were taken for a period of 3-5 minutes as described above.

The ability of test compounds to positively modulate the response (i.e., increase the response) induced by a submaximal concentration of agonist ($EC_{20-30\%}$) such as nicotine is measured. Potentiation is measured based on peak fluorescence responses by screening compounds at fixed concentrations or in a concentration-response manner to derive $EC_{50}$ values. The concentration dependence of changes in fluorescence responses is fitted by nonlinear regression analysis (GraphPad Prism, San Diego, Calif.) to obtain $EC_{50}$ values. The degree of potentiation and $EC_{50}$ values of the test compounds are typically calculated. To enable rank ordering of potency and efficacy, data may be normalized to a reference PAM. In general, compounds of the invention selectively potentiate α4β2 NNRs, but not others including ganglionic receptors expressed in IMR-32 cells. At α4β2 receptors, compounds of the invention typically increase fluorescence responses to submaximal nicotine (considered as 100%) to values ranging from 120 to 500%. The $EC_{50}$ values of active compounds were determined by concentration response analysis ($EC_{50}$) range from about 10 nM to about 100 µM. The data demonstrate the compounds of the invention are α4β2 PAMs that potentiate receptor responses to acetylcholine without themselves triggering receptor activation or desensitization, or either, of the receptor.

Table 1 lists the results for representative compounds of the present invention. The activity (allosteric effects—potentiation of fluorescence responses) ranges are defined as follows; "a" denotes as activity range from 200-400% and "b" denotes an activity range from 150-200%.

TABLE 1

Examples of Selected α4β2 PAMs

| Example No. | Activity | Example No. | Activity |
|---|---|---|---|
| 1 | a | 16 | b |
| 17 | a | 68 | a |
| 29 | b | 25 | b |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (Ia):

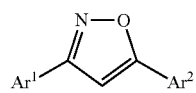

(Ia)

wherein

Ar¹ is heteroaryl, substituted with 0, 1, 2 or 3 substitutions selected from the group consisting of acetyl, alkoxy, alkyl, alkylamino, amino, cyano, halo, haloalkoxy, haloalkyl, hydroxy, and nitro, wherein the heteroaryl is pyrazinyl, or pyrimidinyl;

Ar² is aryl, substituted with 1, 2 or 3 substitutions selected from the group consisting of acetyl, alkoxy, alkyl, alkylamino, amino, halo, haloalkoxy, haloalkyl, and nitro;

or a pharmaceutically acceptable salt thereof.

2. The compound of claim 1, wherein Ar¹ is pyrazinyl.

3. The compound of claim 1, wherein Ar¹ is pyrimidinyl.

4. The compound of claim 1, selected from the group consisting of:

5-(2,4-difluorophenyl)-3-(pyrimidin-5-yl)isoxazole,
3-(pyrimidin-5-yl)-5-(3,4,5-trifluorophenyl)isoxazole,
5-(3,5-difluorophenyl)-3-(pyrimidin-5-yl)isoxazole,
5-(3-fluorophenyl)-3-(pyrimidin-5-yl)isoxazole,
5-(4-bromophenyl)-3-(pyrimidin-5-yl)isoxazole,
5-(4-chlorophenyl)-3-(pyrimidin-5-yl)isoxazole,
5-(3,4-difluorophenyl)-3-(pyrimidin-5-yl)isoxazole,
3-(pyrimidin-5-yl)-5-p-tolylisoxazole,
5-(3,4-dichlorophenyl)-3-(pyrimidin-5-yl)isoxazole,
5-(3-(difluoromethoxy)phenyl)-3-(pyrimidin-5-yl)isoxazole,
5-(4-fluorophenyl)-3-(pyrimidin-5-yl)isoxazole, and
3-(pyrimidin-5-yl)-5-m-tolylisoxazole,
or a pharmaceutically acceptable salt thereof.

5. The compound of claim 1, selected from the group consisting of:

5-(3-chlorophenyl)-3-(pyrazin-2-yl)isoxazole,
5-(3-fluorophenyl)-3-(pyrazin-2-yl)isoxazole,
5-(4-fluorophenyl)-3-(pyrazin-2-yl)isoxazole,
5-(3,4-difluorophenyl)-3-(pyrazin-2-yl)isoxazole,
3-(pyrazin-2-yl)-5-(3,4,5-trifluorophenyl)isoxazole, and
1-(3-(3-(pyrazin-2-yl)isoxazol-5-yl)phenyl)ethanone,
or a pharmaceutically acceptable salt thereof.

6. A compound of formula (Ib)

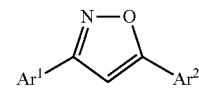

(Ib)

wherein

Ar¹ is heteroaryl, substituted with 0, 1, 2 or 3 substitutions selected from the group consisting of acetyl, alkoxy, alkyl, alkylamino, amino, cyano, halo, haloalkoxy, haloalkyl, hydroxy, and nitro, wherein the heteroaryl is pyridin-3-yl, pyrazinyl, or pyrimidinyl;

Ar² is an aryl, substituted with 2 or 3 substitutions selected from the group consisting of acetyl, alkoxy, alkyl, alkylamino, amino, halo, haloalkoxy, haloalkyl, and nitro or a pharmaceutically acceptable salt thereof.

7. The compound of claim 6, selected from the group consisting of:

5-(3,4-dichlorophenyl)-3-(pyridin-3-yl)isoxazole,
5-(4-fluoro-3-methylphenyl)-3-(pyridin-3-yl)isoxazole,
5-(3-fluoro-4-(trifluoromethoxy)phenyl)-3-(pyridin-3-yl)isoxazole,
5-(3,5-difluorophenyl)-3-(pyridin-3-yl)isoxazole,
5-(3,5-dimethoxyphenyl)-3-(pyridin-3-yl)isoxazole,
5-(2,4-difluorophenyl)-3-(pyridin-3-yl)isoxazole,
5-(3,4-difluorophenyl)-3-(pyridin-3-yl)isoxazole,
5-(3,4,5-trifluorophenyl)-3-(pyridin-3-yl)isoxazole,
or a pharmaceutically acceptable salt thereof.

8. A compound selected from the group consisting of:
5-(3-fluorophenyl)-3-(5-fluoropyridin-3-yl)isoxazole,
5-(4-chlorophenyl)-3-(5-fluoropyridin-3-yl)isoxazole,
5-(4-bromophenyl)-3-(5-fluoropyridin-3-yl)isoxazole,
5-(3,4-dichlorophenyl)-3-(5-fluoropyridin-3-yl)isoxazole,
5-(3,5-difluorophenyl)-3-(5-fluoropyridin-3-yl)isoxazole,
3-(5-fluoropyridin-3-yl)-5-(3,4,5-trifluorophenyl)isoxazole,
3-(5-fluoropyridin-3-yl)-5-(4-fluorophenyl)isoxazole,
5-(4-fluoro-3-methylphenyl)-3-(5-fluoropyridin-3-yl)isoxazole,
3-(5-fluoropyridin-3-yl)-5-(3-(trifluoromethyl)phenyl)isoxazole,
3-(5-fluoropyridin-3-yl)-5-(3-methylphenyl)isoxazole, 5-(3-fluoro-4-(trifluoromethoxy)phenyl)-3-(5-fluoropyridin-3-yl)isoxazole,
3-(3-(5-fluoropyridin-3-yl)isoxazol-5-yl) aniline,
5-(2-chlorophenyl)-3-(5-fluoropyridin-3-yl)isoxazole,
1-(3-(3-(5-fluoropyridin-3-yl)isoxazol-5-yl)phenyl)ethanone,
5-(3-(difluoromethoxy)phenyl)-3-(5-fluoropyridin-3-yl)isoxazole, and
5-(3,5-dimethoxyphenyl)-3-(5-fluoropyridin-3-yl)isoxazole,
or a pharmaceutically acceptable salt thereof.

9. A compound of selected from the group consisting of:
3-(5-chloropyridin-3-yl)-5-(3,4-dichlorophenyl)isoxazole,
3-(5-chloropyridin-3-yl)-5-(2,4-difluorophenyl)isoxazole,
5-(4-chlorophenyl)-3-(5-chloropyridin-3-yl)isoxazole,
3-(5-chloropyridin-3-yl)-5-(3,5-difluorophenyl)isoxazole,
3-(5-chloropyridin-3-yl)-5-(3,4,5-trifluorophenyl)isoxazole,
3-(5-chloropyridin-3-yl)-5-p-tolylisoxazole,
3-(5-chloropyridin-3-yl)-5-(3,4-difluorophenyl)isoxazole,
3-(5-chloropyridin-3-yl)-5-(4-fluorophenyl)isoxazole,
5-(3-chlorophenyl)-3-(5-chloropyridin-3-yl)isoxazole,
3-(5-chloropyridin-3-yl)-5-m-tolylisoxazole,
3-(5-chloropyridin-3-yl)-5-(4-fluoro-3-methylphenyl)isoxazole,
3-(6-chloropyridin-3-yl)-5-(2,4-difluorophenyl)isoxazole, and
5-(3-chlorophenyl)-3-(6-chloropyridin-3-yl)isoxazole;
or a pharmaceutically acceptable salt thereof.

10. A pharmaceutical composition comprising a therapeutically effective amount of the compound of any one of claims 1, 8, 9 and 6, or a pharmaceutically acceptable salt thereof, in a pharmaceutically acceptable carrier.

* * * * *